US012429411B2

(12) United States Patent
Grover et al.

(10) Patent No.: US 12,429,411 B2
(45) Date of Patent: Sep. 30, 2025

(54) METHOD FOR CHARACTERIZING AND IDENTIFYING SUBSTANCES

(71) Applicant: The Regents Of The University Of California, Oakland, CA (US)

(72) Inventors: William H. Grover, Riverside, CA (US); Brittney A. McKenzie, Riverside, CA (US)

(73) Assignee: The Regents Of The University of California, Oakland, CA (US)

( * ) Notice: Subject to any disclaimer, the term of this patent is extended or adjusted under 35 U.S.C. 154(b) by 684 days.

(21) Appl. No.: 17/593,337

(22) PCT Filed: Mar. 17, 2020

(86) PCT No.: PCT/US2020/023173
§ 371 (c)(1),
(2) Date: Sep. 15, 2021

(87) PCT Pub. No.: WO2020/190954
PCT Pub. Date: Sep. 24, 2020

(65) Prior Publication Data
US 2022/0187185 A1 Jun. 16, 2022

Related U.S. Application Data

(60) Provisional application No. 62/820,748, filed on Mar. 19, 2019.

(51) Int. Cl.
*G01N 15/14* (2024.01)
*B01L 3/00* (2006.01)
(Continued)

(52) U.S. Cl.
CPC ........ *G01N 15/14* (2013.01); *B01L 3/502715* (2013.01); *B01L 3/502761* (2013.01);
(Continued)

(58) Field of Classification Search
CPC ........ G01N 15/14; G01N 33/02; G06V 10/62; G06V 10/761; G06V 10/751; G06V 20/698
See application file for complete search history.

(56) References Cited

U.S. PATENT DOCUMENTS

| 6,795,195 B1 | 9/2004 | Barbour et al. | |
| 2002/0159625 A1* | 10/2002 | Elling | C12M 35/02 382/133 |

(Continued)

FOREIGN PATENT DOCUMENTS

| CN | 103528986 A | 1/2014 |
| CN | 107941934 A | 4/2018 |
| WO | WO 2017/186768 A1 | 11/2017 |

OTHER PUBLICATIONS

McKenzie BA, Grover WH. A microfluidic thermometer: Precise temperature measurements in microliter- and nanoliter-scale volumes. PLoS One. Dec. 28, 2017;12(12):e0189430. doi: 10.1371/journal.pone.0189430. (Year: 2017).*

(Continued)

*Primary Examiner* — Ross Varndell
(74) *Attorney, Agent, or Firm* — Hassan Abbas Shakir; Shakir Law PLLC

(57) ABSTRACT

A method for of validating the identity of one of more component(s) in a substance including: obtaining a substance; placing the substance in a plenum with a sealed bottom; exposing the substance to a perturbation; digitally recoding the time-dependent changes in the substance after exposing the substance to the perturbation; producing a chronological fingerprint of the changes, where the chronological fingerprint is a digital multi-dimensional image of the changes as a function of time; and comparing the chronological fingerprint to chronological fingerprints for known substances to validate the one or more component(s)

(Continued)

in the substance being measured. Also described are associated systems and computer program products for implementing the method.

9 Claims, 18 Drawing Sheets

(51) Int. Cl.
 *G06V 10/62* (2022.01)
 *G06V 10/74* (2022.01)
(52) U.S. Cl.
 CPC ............ *G06V 10/62* (2022.01); *G06V 10/761* (2022.01); *B01L 2300/0654* (2013.01); *B01L 2300/1894* (2013.01)

(56) References Cited

U.S. PATENT DOCUMENTS

| | | | | |
|---|---|---|---|---|
| 2005/0246105 | A1* | 11/2005 | Faber | G16B 40/00 702/19 |
| 2007/0253594 | A1* | 11/2007 | Lu | H04N 19/20 382/100 |
| 2014/0137877 | A1 | 5/2014 | Deevi et al. | |
| 2019/0250388 | A1* | 8/2019 | Hillman | G01J 3/36 |
| 2023/0407230 | A1* | 12/2023 | Rao | C12M 47/12 |

OTHER PUBLICATIONS

Extended European Search Report in European Application No. 20773827.9 dated Oct. 28, 2022.
Deng et al., "Microfluidic evaluation of some edible oil quality based on viscosity and interfacial tensions", *International Journal of Food Science and Technology*, 2018, vol. 53, pp. 946-953.
McKenzie et al., "Chronoprints: Identifying Samples by Visualizing How They Change over Space and Time", *ACS Cent. Sci.*, 2019, vol. 5, pp. 589-598.
Araújo et al., "A Fast and Inexpensive Chemometric-Assisted Method to Identify Adulteration in Acai (*Euterpe oleracea*) Using Digital Images", *Food Analytical Methods*, 2018, vol. 11, pp. 1920-1926.
Noda, Isao, "Frontiers of two-dimensional correlation spectroscopy. Part 2. Perturbation methods, fields of applications, and types of analytical probes", *Journal of Molecular Structure*, vol. 1069, 2014, pp. 23-49.
Cuadros-Rodríguez et al., "Chromatographic fingerprinting: An innovative approach for food 'identification' and food authentication—A tutorial", *Analytica Chimica Acta*, vol. 909, 2016, pp. 9-23.
International Search Report and Written Opinion, International Patent Application No. PCT/US2020/023173 issued Jun. 16, 2020.
Examination Report in Australian Application No. 2020241952, dated Nov. 14, 2024 (in 3 pages).
McKenzie B.A. and Grover W.H. (2017) A microfluidic thermometer: Precise temperature measurements in microliter- and nanoliter-scale volumes. PLoS One. Dec. 28, 2017; 12(12): e0189430.

* cited by examiner

METHOD FOR CHARACTERIZING AND IDENTIFYING SUBSTANCES

CROSS REFERENCE TO RELATED APPLICATIONS

This international application claims the benefit of priority to U.S. Provisional Patent Application Ser. No. 62/820,748, filed on Mar. 19, 2019, the contents of which are incorporated by reference in their entirety.

STATEMENT REGARDING FEDERALLY SPONSORED R&D

This invention was made government support under Contract Nos. 1351115, 1353974, 1536026, 1640757, and 1740052 awarded by the National Science Foundation. The Government has certain rights in the invention.

FIELD

Described are methods for identifying chemical substances and associated systems for implementing the methods.

BACKGROUND

Techniques for identifying a substance, or the components in a mixture, have many applications across a wide range of different fields. Such applications include but are not limited to manufacturing quality control, counterfeit detection, purity quantification. Applicable fields include food, beverages, medicine, beauty products, petrochemicals, and energy.

One area of concern is food and the $10 to $15 billion a year global problem of food fraud. See Grocery Manufacturing Association. Consumer product fraud: Deterrence and detection, 21 (2010). In some cases, food ingredients are substituted or diluted with potentially dangerous or toxic alternates, thereby producing a serious public health concern. For example, in 2008 twenty-two food companies in China used the toxic compound melamine, commonly used to produce plastic resins, in infant formula to artificially inflate the apparent protein content of their products resulting in six infant deaths and nearly 300,000 illnesses. Id.; Everstine, K. et al., Economically motivated adulteration (EMA) of food: Common characteristics of EMA incidents., 76 J. Food Prot. 723-35 (2013); Johnson, R., Food fraud and economically motivated adulteration of food and food ingredients, Congressional Research Service, Library of Congress, 40 (2014); Hong, E. et al., Modern analytical methods for the detection of food fraud and adulteration by food category: Adulterated food categories and their analytical methods., 97 J. Sci. Food Agric. 3877-96 (2017). Olive oil was found to be one of the most commonly adulterated food products worldwide between the years 1980 and 2010. See Moore, J. C. et al., Development and application of a database of food ingredient fraud and economically motivated adulteration from 1980 to 2010., 77 J. Food Sci. R118-26 (2012). The University of California, Davis' Olive Center reported in 2010 that 69% of imported olive oils and 10% of California olive oils labeled "extra virgin" did not meet the legal standard. Frankel, E. et al., Tests indicate that imported "extra virgin" olive oil often fails international and USDA standards, Robert Mondavi Institute for Wine and Food Science, University of California, Davis Olive Center, 10 (2010). In some cases, "extra virgin" olive oil is diluted with other less expensive oils such as sunflower seed and peanut oils, which pose serious health risks to individuals who are allergic to these foodstuffs. Johnson, R. et al., supra at 40; Hong, E. et al., supra. at 3877-96. In response to the significant economic and health impact of food fraud, the Grocery Manufacturing Association and the United States Congressional Research Service recommend testing food products during and after their production and suggest that authenticating ingredients is the best way to detect adulteration.

Another area of concern is medicine. It has been found that around 10% of all medications in low- and middle-income countries are counterfeit and may be worthless or even dangerous to patients. Blackstone, E. A. et al., The health and economic effects of counterfeit drugs., 7(4) American Health Drug Benefits 216-24 (2014); World Health Organization. WHO global surveillance and monitoring system for substandard and falsified medical products, 73 (2017). Another example highlighting the need for substance identification techniques is the occasionally confused pharmaceutical ingredients glycerol, which is non-toxic, and diethylene glycol, which is toxic. The accidental or intentional substitution with diethylene glycol has led to hundreds of deaths. In 1937, a chemist at the SE. Massengill Company in Bristol, Tennessee, unwittingly substituted a toxic substance, diethylene glycol, for nontoxic glycerol in a liquid formulation of the early antibiotic sulfanilamide. The resulting medicine, called "Elixir Sulfanilamide," fatally poisoned over 100 persons. See Geiling, E. et al, Pathologic effects of elixir of sulfanilamide (diethylene glycol) poisoning: a clinical and experimental correlation., 111 J. Am. Med. Assoc. 919-26 (1938); Martin, B. J., Elixir: The American tragedy of a deadly drug (Barkerry Press: Lancaster, PA) (2014). The toxicity of diethylene glycol became common knowledge among pharmaceutical companies. However, remarkably, poisonings due to diethylene glycol in medicines remain tragically common today, with a mass poisoning occurring somewhere in the world on average every two years since 1985. Schep, L. J. et al, Diethylene glycol poisoning., 47 Clin. Toxicol. 525-35 (2009). Many of these poisonings occur in resource-limited settings where pharmaceutical companies may not have the resources needed to confirm the identity (and safety) of their manufacturing stocks. The problem of distinguishing diethylene glycol from glycerol is compounded by the fact that they both have very similar properties: they are both transparent, viscous, sweet-tasting liquids, with similar densities, freezing/melting points, and other properties. Consequently, attempts to distinguish diethylene glycol and glycerol by their melting/freezing points alone by using a microfluidic thermometer were unsuccessful. McKenzie, B. A.; Grover, W. H. A microfluidic thermometer: Precise temperature measurements in microliter- and nanoliter-scale volumes., 12 PLoS One No. e0189430 (2017). Simple and inexpensive tools for identifying adulterated drugs can protect consumers from these threats. For example, recent paper-based tests have been developed that can confirm the authenticity of samples of certain drugs. See Weaver, A. A. et al, Paper analytical devices for fast field screening of beta lactam antibiotics and antituberculosis pharmaceuticals., 85 Anal. Chem. 6453-6460 (2013); Koesdojo, M. T. et al., Low-cost, high-speed identification of counterfeit antimalarial drugs on paper., 130 Talanta 122-127 (2014); Boehle, K. E. et al., Paper-based enzyme competition assay for detecting falsified beta-lactam antibiotics., 3 ACS Sensors 1299-1307

(2018). However, there remains an unmet need for simple and low-cost techniques that can be applied to a wide range of different types of drugs.

Still, another area of concern is the petrochemical industry. The addition of solvents is one of the most common practices of adulteration of fuel due to the enormous difference in taxation between gasoline and solvents. G. Mendes et al., Detection and quantification of adulterants in gasoline using distillation curves and multivariate methods, 112 Fuel 163-171 (October 2013). In countries where gasoline is taxed, substitutes such as diesel or kerosene have a lower tax. Id. In addition, gasoline may be adulterated with distillate fuels, industrial solvents, and/or used lubricants. Urban Air Pollution, South Asia Urban Air Quality Management Briefing Note No. 7: Catching Gasoline and Diesel Adulteration, The World Bank (July 2002). The ranges can be small to as much as 20-30% kerosene into fuel. Id. In some scenarios the adulterated fuels increase harmful emissions. In other scenarios, where the octane falls below the vehicle manufacturer's octane requirement, the fuel will cause knocking and physical damage to the engine. In other scenarios, such as the addition to diesel of kerosene subsidized for household low-income use, the diversion of additives deprives a valuable resource from its intended purpose. Id.

Current methods for substance detection include mass spectroscopy, high-performance liquid chromatography, electrochemical analyses, gas-chromatography-mass spectrometry (GC-MS), and destructive methods such as chemical tests. Modern tools of analytical chemistry like GC-MS are unparalleled in their ability to identify a substance or mixture. However, the size, cost, and complexity of these instruments limit their use in important applications in resource-limited settings, and while tools like GC-MS could detect these adulterated substances, these tools are not portable and are not readily available in the poorest regions of the world. Different substances usually have different physical properties. In some cases, by measuring a physical property of a sample and comparing it to a known value for a pure substance, one can possibly chemically identify the sample. For some simple samples, measuring state transition points (freezing/melting point) and density, can be used to identify the sample. However, many natural products, medicines, and other complex mixtures may not have a known freezing point or density. To identify or distinguish samples like these, simple measurements of their physical properties may not be enough. The modern tools of chemistry excel at identifying a sample, but the cost, size, complexity, and power consumption of these instruments often preclude their use in resource-limited settings. Thus, there is a need for an inexpensive and effective means for distinguishing different substances.

SUMMARY

In several embodiments, methods are provided that leverage the way a sample's physical properties change over space and time in order to chemically identify the sample. Under static and homogeneous conditions, a sample's properties usually remain unchanged, so embodiments disclosed herein involve inducing a change in the substance by perturbing it in some way. This perturbation could take many different forms, for example a rapidly changing temperature gradient to perturb the samples. Different samples react to this perturbation in different ways (for example, in a temperature gradient, different samples might freeze, or thaw, or separate into their components, or change in other ways).

Additionally, these changes can occur at different locations in different samples (if the perturbation is applied across the sample as a gradient of some sort) and at different times in different samples (if the perturbation is changing over time). The resulting multidimensional data set of how a sample changes over space and time in response to a perturbation can serve as a "fingerprint" to identify the sample.

If a perturbation can be consecutively applied to samples in a consistent manner, then a specific sample's resulting "fingerprint" should be conserved for a given sample and the fingerprint can be stored in a database and used to identify the same sample in the future.

Some embodiments relate to a method for identifying one or more substances, where the method can comprise: (1) obtaining a substance; (2) placing the substance in a plenum with a sealed bottom; (3) exposing the substance to a perturbation; (4) digitally recoding the time-dependent changes in the substance after exposing the substance to the perturbation; (5) producing a chronological fingerprint of the changes, where the chronological fingerprint can be a digital multi-dimensional image of the changes as a function of time; and (6) comparing the chronological fingerprint to chronological fingerprints for known substances to determine the substance being measured. In some methods, the step of comparing can comprise comparing the chronological fingerprint to chronological fingerprints for known substances via feature tracing, image differences, or image hashing. For some methods, the known substances can comprise known substances measured in the same experiment. In some method embodiments, the known substances can comprise known substances previously measured, form a database of chronological fingerprints. With some embodiments, the known substances can comprise both known substances measured in the same experiment and known substances previously measured, e.g., from a database of chronological fingerprints.

Some embodiments can describe a system for identifying one or more substances. The system can comprise: (1) a fluidic chip defining one or more plena with a sealed bottom where a substance can be inserted into one or more plenum; (2) a mechanism for applying a perturbation to the one or more plena; (3) an optical sensor for capturing the response of the substance when the fluidic chip is exposed to the perturbation; and (4) a processor for producing a chronological fingerprint from the response of the substance, where the chronological fingerprint is a digital image of the response of the substance to the perturbation as a function of time, and then comparing the chronological fingerprint of the substance to one or more chronological fingerprints of known substances to identify the substance. For some systems, the fluidic chip can comprise multiple plena with sealed bottoms, where a plurality of substances can be optionally be tested, one in each plenum.

In some embodiments, the perturbation can comprise a thermal perturbation, a force perturbation, or a physical perturbation. With some system embodiments, the mechanism for applying a thermal perturbation can comprise an apparatus that can contain a thermal perturbation substance, the apparatus defining a chamber for storing the thermal perturbation substance, where when characterization is initiated, the thermal perturbation substance can be placed in heat-transfer communication with part of the fluidic chip containing the one or more plena. With some systems, the mechanism for applying a force perturbation can comprise an apparatus for exerting a force on the fluidic chip. In some systems, the mechanism for applying a physical perturbation can comprise one or more chambers for storing perturbation particles, and one or more particles that would be dropped into the substance in the plenum. For some systems, the particles can comprise spheres of poly-epoxide, polyvinyl alcohol (PVA), low density polyethylene (LDPE), high density polyethylene (HDPE), polycarbonate (PC), polystyrene (PS), polypropylene (PP), polyurethane, polytetrafluoroethylene (PTFE), polyvinyl chloride (PVC), polyamide (Nylon), polyethylene glycol (PEG), polyethylene terephthalate (PET), polybutylene terephthalate (PBT), polytrimethylene terephthalate, polyethylene naphthalate, polymethylmethacrylate (PMMA or acrylic), poly-epoxide, polyoxymethylene (POM or acetal), acrylonitrile butadiene styrene (ABS), polyglycolic acid, polylactic acid, polycaprolactone, polyhydroxyalkanoate, polyhydroxybutyrate, polyethylene adipate, polybutylene succinate, or poly(3-hydroxybutyrate-co-3-hydroxyvalerate), plastic, wood, metals and their alloys and oxides (e.g., silicon, titanium, copper, silver, gold, platinum, aluminum, stainless steel, steel, brass, bronze), or a mixture thereof. In some embodiments, the particles can comprise steel spheres.

With some systems, the processor can compare the chronological fingerprint of the substance to a stored chronological fingerprint of a known substance. In some embodiments, the processor can compare the chronological fingerprints of the plurality of substances to each other, the plurality of substances can consist of unknown substances, known substances, or both known and unknown substances. In some systems, the processor can further compare the chronological fingerprints of the plurality of substances to a stored chronological fingerprint of a known substance. For some systems, the relative position of the fluidic chip and the optical sensor can be the same for each measurement. For some systems, the optical sensor can be used to track the location of one or more particles inside one or more plena on the chip.

In some embodiments, a computer program product can be described. Some computer program products can comprise a non-transitory computer usable medium having computer readable code embodied therein for identifying a substance, which comprises the steps of: (1) obtaining one or more time-dependent perturbations of one or more substances; (2) producing a chronological fingerprint of the sample experiencing the perturbation, where the chronological fingerprint can be a multi-dimensional digital image of the response of the sample as a function of time; and (3) comparing the chronological fingerprint of the sample measured to chronological fingerprints of one or more known samples, either in the same experiment, each sample measured either in the same experiment or from a database of chronological fingerprints, to determine the substance being measured. Some computer program products can further comprise the step of converting the chronological fingerprint to a binary chronological fingerprint before comparing. In some computer product embodiments, the product further comprises the step of tracing the features of the binary chronological fingerprint before comparing, where the comparing is done on the traced features. For some computer program products, the product can further comprise the step of calculating the sum of the pixel-by-pixel differences between two chronological fingerprints.

Some examples relate to a method of validating the identity of one or more component(s) in a substance, including:
(1) obtaining the substance;
(2) placing the substance in a plenum with a sealed bottom;
(3) exposing the substance to a perturbation;
(4) digitally recoding the time-dependent changes in the substance after exposing the substance to the perturbation;
(5) producing a chronological fingerprint of the changes, where the chronological fingerprint is a digital multi-dimensional image of the changes as a function of time; and
(6) comparing the chronological fingerprint to chronological fingerprints for known substances to validate the one or more component(s) in the substance being measured.

In some examples, the step of comparing includes comparing the chronological fingerprint to chronological fingerprints for known substances via feature tracing, image differences, or image hashing.

In some examples, the known substances include known substances measured in the same experiment.

In some examples, the known substances include known substances previously measured, form a database of chronological fingerprints.

In some examples, the known substances include both known substances measured in the same experiment and known substances previously measured, from a database of chronological fingerprints.

Some examples relate to a system for validating one or more components in a substance including:
(1) a fluidic chip defining one or more plena with a sealed bottom where a substance is inserted into a first plenum;
(2) a mechanism for applying a perturbation to the one or more plena;
(3) an optical sensor for capturing the response of the substance when the fluidic chip is exposed to the perturbation; and
(4) a processor configured to:
produce a chronological fingerprint from the response of the substance, where the chronological fingerprint is a digital image of the response of the substance to the perturbation as a function of time, and then comparing the chronological fingerprint of the substance to one or more chronological fingerprints of known substances to validate the one or more component(s) in the substance.

In some examples, the fluidic chip includes multiple plena with sealed bottoms, where a plurality of substances is optionally tested, one in each plenum.

In some examples, the perturbation includes a thermal perturbation, a force perturbation, or a physical perturbation.

In some examples, the mechanism for applying a thermal perturbation includes an apparatus containing a thermal perturbation substance, the apparatus defines a chamber for storing the thermal perturbation substance, where when characterization is initiated, the thermal perturbation substance is placed in heat-transfer communication with part of the fluidic chip containing the one or more plena.

In some examples, the mechanism for applying a force perturbation includes an apparatus for exerting a force on the fluidic chip.

In some examples, the mechanism for applying a physical perturbation includes a one or more chambers for storing perturbation particles, and one or more particles that would be introduced into the substance in the plenum.

In some examples, the particles include spheres of poly-epoxide, polyvinyl alcohol (PVA), low density polyethylene (LDPE), high density polyethylene (HDPE), polycarbonate (PC), polystyrene (PS), polypropylene (PP), polyurethane, polytetrafluoroethylene (PTFE), polyvinyl chloride (PVC), polyamide (Nylon), polyethylene glycol (PEG), polyethylene terephthalate (PET), polybutylene terephthalate (PBT), polytrimethylene terephthalate, polyethylene naphthalate, polymethylmethacrylate (PMMA or acrylic), poly-epoxide, polyoxymethylene (POM or acetal), acrylonitrile butadiene styrene (ABS), polyglycolic acid, polylactic acid, polycaprolactone, polyhydroxyalkanoate, polyhydroxybutyrate, polyethylene adipate, polybutylene succinate, or poly(3-hydroxybutyrate-co-3-hydroxyvalerate), plastic, wood, metals and their alloys and oxides (e.g., silicon, titanium, copper, silver, gold, platinum, aluminum, stainless steel, steel, brass, bronze), or a mixture thereof.

In some examples, the particles include steel spheres.

In some examples, the processor compares the chronological fingerprint of the substance to a stored chronological fingerprint of a known substance.

In some examples, the processor compares the chronological fingerprints of the plurality of substances to each other, the plurality of substances consisting of unknown substances, known substances, or both known and unknown substances.

In some examples, the processor further compares the chronological fingerprints of the plurality of substances to a stored chronological fingerprint of a known substance.

In some examples, relative position of the fluidic chip and the optical sensor are the same for each measurement.

In some examples, the optical sensor is used to track the location of one or more particles inside one or more plena on the chip.

Some examples relate to a computer program product including a non-transitory computer usable medium having computer readable code embodied therein for validating one or more component(s) in a substance, which comprises the steps of:

(1) obtaining one or more time-dependent perturbations of one or more substances;
(2) producing a chronological fingerprint of the sample experiencing the perturbation, where the chronological fingerprint is a multi-dimensional digital image of the response of the sample as a function of time;
(3) comparing the chronological fingerprint of the sample measured to chronological fingerprints of one or more known samples, each sample measured either in the same experiment or from a database of chronological fingerprints, to validate the one or more components in the substance being measured.

In some examples, the computer program product further includes a step of converting the chronological fingerprint to a binary chronological fingerprint before comparing.

In some examples, the computer program product further includes a step of tracing the features of the binary chronological fingerprint before comparing, where the comparing is done on the traced features.

In some examples, the computer program product further includes a step of calculating the sum of the pixel-by-pixel differences between two chronological fingerprints.

These and other examples are described in greater detail below.

DETAILED DESCRIPTION

As used herein, the term "substantially" is to be understood in the context of the analytical techniques used to show the uniformity of a property or characteristic. The term, therefore, is defined to include uniform properties showing less than 10% of divergence between the local property and average bulk property, and preferably, less than 5% of divergence between the local property and average bulk property.

Method for Identifying a Substance

Figure 1:
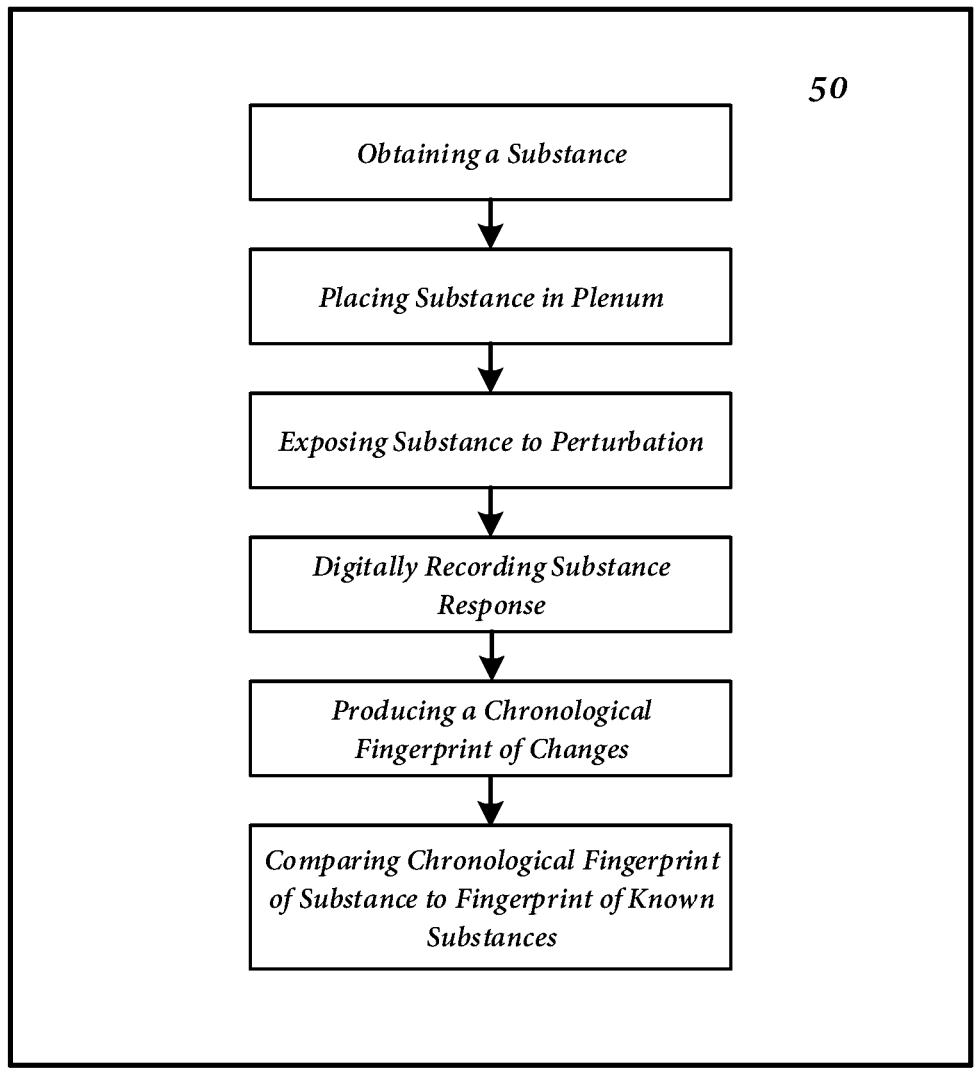
FIG. 1. An example embodiment of a method for identification of a substance by examining a "chronological fingerprint," or "chronoprint," of the substance and chronological fingerprints of known substances.

In several embodiments, a method for identifying one or more substances is provided. The substances can be solids, liquids, aqueous mixtures, powders, slurries, suspensions, or any substances that can undergo a change, such as a phase change, a chemical separation, or a physical separation, in response to changing temperature. In some embodiments, the response is a visual response. In some embodiments, the response is not visually apparent but can be captured with the addition of a visually apparent physical perturbation, e.g., particles, for visualization. In some embodiments, the method can comprise: (1) obtaining a substance; (2) placing the substance in a plenum with a sealed bottom; (3) exposing the substance to a perturbation; (4) digitally recoding the time-dependent changes in the substance after exposing the substance to the perturbation; (5) producing a chronological fingerprint of the changes, where the chronological fingerprint is a digital multi-dimensional image of the changes as a function of time; and (6) comparing the chronological fingerprint to chronological fingerprints for known substances to determine the substance being measured. A non-limiting example of such a method, 50, is shown in FIG. 1.

Placing the Substance in a Plenum

In some embodiments, the step placing the substance in a plenum through an inlet can comprise introducing the substance into the plenum until it is filled partially or completely, such that the substance filled the portion of the plenum can be recorded. In some embodiments, multiple plena can be compared concurrently, where the plena are placed in parallel, such as in a fluidic chip. In such embodiments, different substances can be placed into the plena, one substance per plenum.

Exposing the Substance to a Perturbation

In some embodiments, the step of exposing the substance to a perturbation can comprise introducing a perturbation that changes the thermodynamic equilibrium of the substance. In some embodiments, the step of applying a perturbation can comprise applying a thermal perturbation, a force perturbation, or a physical perturbation. In some embodiments, multiple types of perturbations can be done in parallel (e.g., a thermal perturbation and a physical perturbation).

In some embodiments, the step of applying a thermal perturbation can comprise placing a thermal perturbation substance in thermal communication with one or more plena holding the substances, such that all plena being concurrently tested are in substantially the same thermal communication, or heat transfer. For example, a fluidic chip defining one or more plena of with a uniform initial temperature can be dipped into a thermal perturbation substance of a second, different temperature, such that each plenum is similarly exposed to the thermal perturbation substance at the second temperature. In some steps, the step of placing a thermal perturbation substance can comprise placing cryogenic substances (e.g., liquid nitrogen, liquid nitrogen and ethanol, dry ice, dry ice and acetone, dry ice and 2-propanol, dry ice and acetonitrile, and the like), water-based substances (ice, ice and calcium chloride hexahydrate, ice and sodium chloride, boiling water), mineral oil, silicone oil, hydrocarbon substances (e.g., Freon), liquids or gases undergoing a phase change (e.g., refrigerants, 1,1-difluoroethane, 1,1,1-trifluoroethane, 1,1,1,2-tetrafluoroethane), or heating/cooling plates (e.g., metal plates, electric or combustion heaters, thermoelectric or Peltier coolers). In some embodiments, the heating/cooling plates may be heated or cooled separately from the plena (using e.g. a refrigerator, freezer, oven, or any of the aforementioned methods) before the plates are brought into thermal communication with the plena. In some embodiments, the thermal perturbation may be provided by placing the plenum into an environment that provides the thermal perturbation (e.g. a refrigerator, freezer, oven, or any of the aforementioned methods). In some embodiments, the plena are incorporated into the thermal perturbation substance (using e.g. channels inside heating/cooling plates or thermoelectric/Peltier coolers) to facilitate thermal communication between the plena and the thermal perturbation substance. In some methods, the step of placing a thermal perturbation substance in thermal communication with one or more plena can comprise placing liquid nitrogen in thermal communication with one or more plena. The change can be cooling or freezing, as well as for heating or boiling.

For some methods, the step of applying a force perturbation can comprise applying a change in force to the fluidic chip. Examples of applying a force can be by changing the direction of gravity (e.g., tilting the fluidic chip to manipulate the axis of gravity, exposing the fluidic chip to an impulse force, such as on an acceleration table, or applying a periodic force).

In some embodiments, the step of applying a physical perturbation can comprise exposing one or more particles to a substance within the plenum. In some embodiments, where multiple samples are being measured in parallel, the substances in each plenum are exposed to the same types of particles so that their reaction can be characterized in parallel. While not wanting to be limited by theory, the particles can be used to measure viscosity of the substance. In some steps, the particles can be pyramidal, cubic, or spherical. In some steps, the particles can be spherical pellets. In some steps, the step of adding one or more particles can be comprised adding a particle comprising poly-epoxide, polyvinyl alcohol (PVA), low density polyethylene (LDPE), high density polyethylene (HDPE), polycarbonate (PC), polystyrene (PS), polypropylene (PP), polyurethane, polytetrafluoroethylene (PTFE), polyvinyl chloride (PVC), polyamide (Nylon), polyethylene glycol (PEG), polyethylene terephthalate (PET), polybutylene terephthalate (PBT), polytrimethylene terephthalate, polyethylene naphthalate, polymethylmethacrylate (PMMA or acrylic), poly-epoxide, polyoxymethylene (POM or acetal), acrylonitrile butadiene styrene (ABS), polyglycolic acid, polylactic acid, polycaprolactone, polyhydroxyalkanoate, polyhydroxybutyrate, polyethylene adipate, polybutylene succinate, or poly(3-hydroxybutyrate-co-3-hydroxyvalerate), plastic, wood, metals and their alloys and oxides (e.g., silicon, titanium, copper, silver, gold, platinum, aluminum, stainless steel, steel, brass, bronze), or a mixture thereof.

While not wanting to be limited by theory, it is thought that the velocity of a particle passing through a sample is a function of the particle's properties (e.g., size, density), the sample's properties (e.g., viscosity, density), and the force applied to the particle (e.g., 1 g if using Earth's gravitational acceleration, or more if using artificial acceleration, such as centrifugal acceleration). For spherical particles, this relationship can be described by Stokes' Law. In practice, the size and density of particles are likely constant over the course of an experiment, but the viscosity and density of the samples may vary from one sample to another; this variance will result in different digital images for the different samples that can be used to chemically distinguish between samples.

While not wanting to be limited by theory it is thought that the density of the particles should be chosen such that they would travel through the substances to provide a graphical representation that is influenced by the sample viscosity and sample density. In some embodiments, the substance can be exposed to a plurality of particles, each with a different density, with the different particles in different plena, such that the variation on density can also be observed in the resulting chronological fingerprints.

Some particles are chosen such that the particles will "fall" through all a sample; this implies that the particle is denser than its surrounding sample. This embodiment gives rise to a digital image with a particle trajectory that has a negative slope. However, this technique is not limited to particles with densities greater than the sample density. Particles could also be used that are less dense than the surrounding sample and float up from a release point. This type of embodiment would give rise to a digital image with a particle trajectory that has a positive slope. The "particle" could even be a bubble or droplet of immiscible fluid whose position is detectable in the channel Finally, particles could also be used that are equal in density to the surrounding sample; this would give the particle a zero buoyant mass and cause the particle to remain stationary in the channel (resulting in a flat line in the sample's chronological fingerprint). It should be noted that while particle densities can be manipulated, the properties of a substance do not need to be known before characterization. This method allows for the comparison of unknown responses to known responses in fact the properties for complex samples will not be readily known.

In some samples, it is thought that if a perturbation applied to the sample, for example a temperature gradient or a gravitational acceleration, a density gradient and/or viscosity gradient are created within the sample, and the velocity of a particle will vary as it travels through that sample. The particle's velocity may decrease as it enters a substance region similar to the particle's density; the particle may even stop moving if it reaches a substance region with exactly the same density as the particles, it becomes neutrally buoyant. Additionally, the particle's velocity may decrease as it enters a substance region with higher viscosity, or increase as it enters a substance region with lower viscosity. Other changes in the sample could also cause a particle to stop moving or even reverse the direction of motion, such as such as a liquid sample freezing, or a growing solid-liquid interface that physically displaces the particles from the solid sample. This substance's unique behavior would be captured in the digital image and can be used as the basis for distinguishing between different samples.

In some embodiments, a plurality of particles of different characteristics, e.g., densities or sizes, can be added to the same plenum, with their initial order of addition proceeding with decreasing/increasing density and/or size so that they would not initially travel past each other. Substance measurements can either be taken concurrently or recorded and compared. In some embodiments, the particles can be chosen such that they are density-neutral to the known substances to inspect the substance being characterized versus a known density. The paths followed by the different particles can then be distinguished in the resulting digital image by using their different sizes, colors, etc., then the resulting digital image would contain not just one but many different particle paths, each adds additional information and additional discrimination power to the aforedescribed technique.

In some embodiments, the step of applying a perturbation can comprise applying a thermal perturbation and a physical perturbation. In this embodiment, a thermal perturbation is initiated and when a thermal gradient has developed along the plena, a physical perturbation is initiated. While not wanting to be limited by theory, it is thought that during a thermal perturbation, a temperature gradient can be created along the length of the plena and since a substance's viscosity and density are also a function of the substance's temperature a particle travelling a substance during the thermal perturbation would experience a velocity change as the particle passes through the substance. In practical terms, this means that a bead dropped though the plenum will speed up and slow down, or even stop or reverse at different points within the substance sample due to the changes in substance's material properties. In addition, the thermal gradients within the substance are functions of the substances' thermal conductivity, Reynolds number, and Prandtl number, since the geometry and thermal conductivity of the fluidic chip is the same, the thermal gradient within the substance may differ for chemically different substances resulting in varying particle behavior. Overall, the combination of thermal and physical perturbations results in a complex path followed by the particle in the substance's digital image, a path that is dictated not only by the substance's viscosity, density and material properties, but also how those properties change as a function of temperature. Such a characterization adds significant discrimination power: in the unlikely event that two different substances have the same viscosity and density at one temperature, their digital images can still distinguish the two substances based on how their viscosities and densities change at different temperatures.

Digitally Recording the Response of the Substance

In some methods, the step of digitally recoding the time-dependent changes in the substance after exposing the substance to the perturbation can comprise digitally recording the behavior of the substance after the initiation of the perturbation to see the substance's response. In some embodiments, the digitally recording can be done from a time right before the perturbation is initiated, or if multiple perturbations right before the first perturbation, until a time where sufficient response has been recorded to distinguish between samples. In some embodiments, the response is recorded until the overall response optical variation is less than 10%/second, where the variation is determined from comparing the digital image from 1 second prior to the current image and examining the variation. For some methods, the step of digitally recording the changes can comprise digitally recording the substances in one or more plena with a digital image sensor, such as a digital camera. In some embodiments, the digital image sensor can be provided by a smartphone camera or other separate camera that is interfaced with the system.

Producing a Chronological Fingerprint

For some methods, the step of producing a chronological fingerprint of the changes comprises digitally stitching the response of each plenum as a function of time to create a plot of the response as a function of time. The chronological fingerprint can be a multi-dimensional digital image of the changes as a function of time, such as a bitmap, jpeg, png, gif, or other image format known in the art. Digitally stitching the response of the plenum can be done by methods known in the art for combining time dependent responses to create plots. While not wanting to be limited by theory, using a multi-dimensional image, e.g., a 2-D array of pixels, instead of a line plot provides more information than a plot alone and allows for further discrimination between substances that may be otherwise indistinguishable by a plot alone.

Some possible methods for digitally stitching the response of each plenum as a function of time can comprise creating a data set where single frame of the video is X-Y plane (with Y aligned with the channel axis) and then stacking multiple frames as a function of time in the Z dimension to create a three-dimensional dataset. Then, the data set can be re-sliced by selecting a pre-determined Y-coordinate to selects a longitudinal sample from the plenum as a function of time, a Y-Z slice that shows plenum distance along the vertical axis and time along the horizontal axis. Alternatively, in some methods, each X pixel for every Y location can be averaged into a single Y pixel to convert the entire plenum into a single column of pixels.

Comparing the Fingerprint to Other Fingerprints

With some method embodiments, the step of comparing the chronological fingerprint to chronological fingerprints for known substances to determine the substance being measured can be done by using image processing methods known in the art to compare differences between multiple images. Some steps can comprise comparing chronological fingerprints of concurrently measured substances, known/control versus unknown. Other embodiments, the comparing step can comprise comparing a chronological fingerprint of a measured substance to a chronological fingerprint stored in a database. Yet other steps can comprise comparing the chronological fingerprint from a substance to both stored chronological fingerprints and concurrently measured chronological fingerprints of known substances. In some steps, the substance can be determined by using image processing to exclude dis-similar chronological fingerprints. While not wanting to be limited by theory, when a perturbation, like a dynamic temperature gradient, is applied to the plena, each substance sample receives the same perturbation at the same point in space and time. If two substances in the same experiment display similar chronological fingerprints, or changes over space and time in response to the perturbation, the similar behavior suggests that the samples may be the same. However, if two samples display significantly different chronological fingerprints, then this proves that the samples are different.

In some methods, the image processing methods used to determine differences between the chronological fingerprints can be methods known in the art. Some non-limiting example methods are feature tracing, image differences, and image hashing. Feature tracing reduces the chronological fingerprints to curves that can be directly compared. Image differences calculates the sum of the pixel-by-pixel differences between two chronological fingerprints. Image hashing converts each chronological fingerprint into a 64-bit representation that is further analyzed for differences.

In some methods, the step of comparing the substance chronological fingerprint to chronological fingerprints to determine the substance can comprise of identifying the substance when the difference between the substance fingerprint and a known substance's fingerprint is less than about 20%, about 15%, about 10%, about 7%, or about 5%, as determined by image matching techniques known in the art. In some embodiments, the difference between the substance fingerprint and a known substance's fingerprint is about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% or 95%.

Substance Identification System

Figure 2:
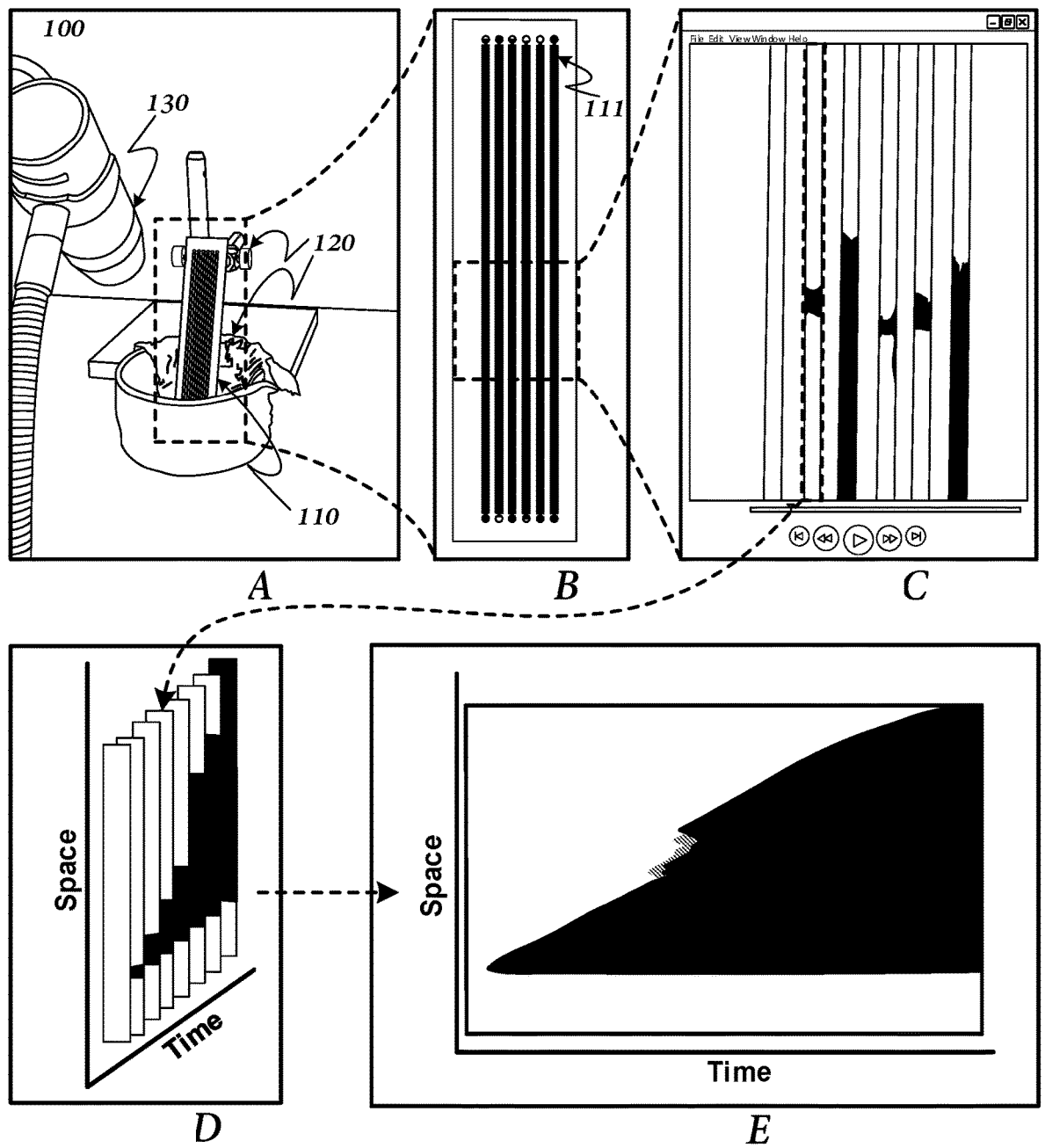
FIG. 2. Producing a chronological fingerprint, capturing how six samples, in this example, authentic and adulterated samples of an over-the-counter liquid cold medicine, respond to a perturbation over space and time, in this case a rapidly changing temperature gradient. (A) A microfluidic thermometer chip containing the samples is partially immersed in liquid nitrogen to establish a rapidly changing temperature gradient along the chip. (B) The chip contains six samples (colored black) loaded in microfluidic channels that run parallel to the dynamic temperature gradient. (C) A video input device (e.g., a USB camera) records a video of the physical changes in the samples as they react to the dynamic temperature gradient. (D) For each sample, a MATLAB code executing on a processor extracted an image of the entire channel from each frame of the video. (E) By reducing each channel image to a single column of pixels, and then placing these columns side-by-side, a bitmap image was created (the sample's chronological fingerprint or chronoprint) that captures how the sample changes over space (the y-axis) and time (the x-axis). Finally, by comparing the chronological fingerprints of all six samples in the chip to each other or to reference chronoprints from a database, it can be determined whether the samples are either likely the same or different.

In the present invention, a system for identifying one or more substances can be described. The substance identification system can comprise a fluidic chip defining one or more plena, a mechanism for applying a perturbation to the one or more plena, an optical sensor for recording the response of the substance when the fluidic chip is exposed to the perturbation, a processor for producing a chronological fingerprint of the response of the substance and comparing the chronological fingerprint of the substance to one or more chronological fingerprints of known substances to identify the substance, where the chronological fingerprint is a multi-dimensional digital image of the response of the substance as a function of time. One possible example of such a system, 100, is depicted in FIG. 2 (A), where the fluidic chip, 110, is placed in a mechanism for applying a thermal perturbation, 120, and an optical sensor, 130, to recording the response, FIG. 2 (C), for the processor, 140, not shown for clarity. In FIG. 2 (B), a detailed view of the fluidic chip, 110, reveals plena, 111; with this specific embodiment having six plena. As shown in FIG. 2 (D), the recorded response can be digitally processed by a processor (not shown), 140, to produce a chronological fingerprint, FIG. 2 (E).

Fluidic Chip

In some system embodiments, the fluidic chip can define one or more plena. In some embodiments, the one or more plena can be elongated plena. In some embodiments, the plena can be in parallel. In some embodiments, the system can be setup in such a manner as to compare the behavior of the substance being measured to a pre-recorded database of behaviors of a known substance. In some systems, the behavior of the substance being measured can be compared to the behavior of one or more known substances, each substance in its own plenum concurrently being measured. For some embodiments, the behaviors of a substance can be compared to multiple known or control substances in a plurality of plena, each on its own plenum concurrently being measured. In some systems, the behaviors of multiple substances to be measured can be compared against one or more known or control substances, each in their own plenum concurrently being measured. In some embodiments, the behaviors of the known substances can be pre-recorded database of behaviors of a known substance, concurrently being measured, or a combination thereof.

In some chips, the plena can be characterized as channels, or tubes, having a sealed bottom. In some embodiments, the sealed bottom can be sealed temporarily such that substances being measured can be inserted or extracted from the plena but then held in place during characterization. Examples of temporary seals can comprise valves, plugs, and the like. In some embodiments, the sealed bottom can be sealed permanently, such as where the diameter of the plena is large enough to allow fluid to fill the bottom of the plena and to let air escape. In some embodiments, the representative diameter of the plena can range from about 10 µm, about 20 µm, about 30 µm, about 40 µm, about 50 µm, about 60 µm, about 70 µm, about 80 µm, about 90 µm, about 100 µm, about 150 µm, about 200 µm, about 250 µm, about 300 µm, about 350 µm, about 400 µm, about 450 µm, about 488 µm, about 500 µm, about 550 µm, about 600 µm, about 700 µm, about 750 µm, about 1 mm, about 2 mm, about 3 mm, about 4 mm, about 5 mm, about 7.5 mm, about 10 mm, about 15 mm, about 25.4 mm, to about 50.8 mm, or any combination thereof, such as about 488 µm. In some embodiments, the representative diameter of the plena can be about 2 mm. The representative diameter is calculated by determining the diameter for a representative circle that has the same area as the cross-section of the plena.

Mechanism for Applying a Perturbation

In some systems, the mechanism for applying the perturbation to the one or more plena can be implemented such that the perturbation is applied uniformly across to all plena. In some embodiments, the mechanism can comprise a mechanism for applying a thermal perturbation, a mechanism for applying a force perturbation, a mechanism for applying a physical perturbation, or a combination thereof.

In some systems, the mechanism for applying a thermal perturbation comprise an apparatus that contains a thermal perturbation substance, where the apparatus defines a chamber for storing the thermal perturbation substance, where when characterization is initiated, the thermal perturbation substance is placed in heat-transfer communication with one end of the fluidic chip containing the sealed ends of one or more plena. In some embodiments, the thermal perturbation substance can be a controlled temperature that is different than the initial temperature of the substances being characterized. In some embodiments, the thermal perturbation substance can comprise cryogenic substances (e.g., liquid nitrogen, liquid nitrogen and ethanol, dry ice, dry ice and acetone, dry ice and 2-propanol, dry ice and acetonitrile, and the like), water based substances (ice, ice and calcium chloride hexahydrate, ice and sodium chloride, boiling water), mineral oil, and silicone oil, hydrocarbon substances (e.g., Freon), or heating/cooling plates (metal). In some embodiments, the heating/cooling plates may be heated or cooled separately from the plena (using e.g. a refrigerator, freezer, oven, or any of the aforementioned methods) before the plates are brought into thermal communication with the plena. In some embodiments, the thermal perturbation may be provided by placing the plenum into an environment that provides the thermal perturbation (e.g. a refrigerator, freezer, oven, or any of the aforementioned methods). In some embodiments, the plena are incorporated into the thermal perturbation substance (using e.g. channels inside heating/cooling plates or thermoelectric/Peltier coolers) to facilitate thermal communication between the plena and the thermal perturbation substance. In some embodiments, the mechanism for applying a thermal perturbation can comprise a chamber and an apparatus for supporting the fluidic chip where the bottom of the fluidic chip is dipped into the thermal perturbation substance. In some systems, the mechanism for applying a thermal perturbation can comprise a heat exchanger where the thermal perturbation substance at a controlled temperature is circulated through the exchanger and when characterization is initiated, where the exchanger is placed in thermal communication with the fluidic chip, such as by physically touching the fluidic chip to the heat exchanger. Non-limiting examples of heat exchangers are present in a refrigerator, a dilution refrigerator, or a Dewar cooler. In some embodiments, the mechanism for applying a thermal perturbation can comprise a heating/cooling plate maintained at a controlled temperature. In some embodiments the heating/cooling plate can be part of a thermoelectric device, such as a Peltier cooler. While not wanting to be limited by theory it is thought that thermal gradients, especially rapidly changing temperature gradients, can induce phase changes, separations, and other changes within the samples that may be used to distinguish between substances. The change can be cooling or freezing, as well as for heating or boiling.

In some embodiments, the mechanism for applying a force perturbation can comprise an apparatus for exerting a force on the fluidic chip. Examples of apparatuses for exerting a force on the fluidic chip can comprise an acceleration table, piston actuator, hydraulic actuation, electromagnetic actuator, a piezoelectric actuator, a spring (e.g., leaf/bow, coil, helical, torsion, volute), a centrifuge, a simple pivot where the orientation of the fluidic chamber is changed (e.g., from horizontal to vertical or from vertical to horizontal) such that the direction vector of gravitational force is uniformly changed. One possible embodiment would be placing the fluidic chip on a pivot such that the orientation of the plena with respect to the gravitational vector can be manipulated, i.e., the chip can be tilted. While not wanting to be limited by theory, it is thought that for heterogeneous samples containing suspended solids, changing the gravitational acceleration may yield unique responses.

In some embodiments, the mechanism for applying a physical perturbation can comprise one or more chambers for storing perturbation particles, and one or more particles that would be introduced into the substance in the plenum. In some embodiments, each plenum would have its own chamber which can be activated at the same time to release the particles. In other embodiments, trapping features within each plenum would retain the particles within the channel during sample addition and removal. While not wanting to be limited by theory, the particles can be used to measure viscosity and density of the substance. In some embodiments, the particles can be pyramidal, cubic, or spherical. In some systems, the particles can be spherical pellets. In some embodiments, the particles can be comprised of poly-epoxide, polyvinyl alcohol (PVA), low density polyethylene (LDPE), high density polyethylene (HDPE), polycarbonate (PC), polystyrene (PS), polypropylene (PP), polyurethane, polytetrafluoroethylene (PTFE), polyvinyl chloride (PVC), polyamide (Nylon), polyethylene glycol (PEG), polyethylene terephthalate (PET), polybutylene terephthalate (PBT), polytrimethylene terephthalate, polyethylene naphthalate, polymethylmethacrylate (PMMA or acrylic), poly-epoxide, polyoxymethylene (POM or acetal), acrylonitrile butadiene styrene (ABS), polyglycolic acid, polylactic acid, polycaprolactone, polyhydroxyalkanoate, polyhydroxybutyrate, polyethylene adipate, polybutylene succinate, or poly(3-hydroxybutyrate-co-3-hydroxyvalerate), plastic, wood, metals and their alloys and oxides (e.g., silicon, titanium, copper, silver, gold, platinum, aluminum, stainless steel, steel, brass, bronze), or a mixture thereof.

With some systems, the perturbation particles can define a representative diameter that is smaller than the plenum's dimensions such that the passage of the particle through the substance is unimpeded by the sides of the plenum, where the representative diameter is calculated by determining the diameter for a representative sphere that has the same volume as the volume of the plena. In some systems, the representative diameter of the one or more particles range from about 1 μm, about 5 μm, about 10 μm; about 15 μm; about 20 μm; about 25 μm, about 30 μm; about 35 μm; about 40 μm; about 45 μm; about 50 μm, about 60 μm; about 70 μm; about 80 μm; about 90 μm; about 100 μm; about 125 μm, about 150 μm; about 200 μm; about 250 μm, about 300 μm; about 375 μm, about 400 μm; about 450 μm; about 500 μm, about 750 μm; about 1 mm, about 1.5 mm, about 2 mm, about 2.5 mm, about 3.75 mm, about 5 mm, about 7.5 mm, about 12.7 mm, to about 25.4 mm, or any combination thereof, such as about 793.75 μm or 1/32-inch.

In some systems, the mechanism for applying the perturbation can comprise a combination of thermal perturbation, force perturbation, or physical perturbation. For example, the coefficient of thermal expansion for a substance can be exploited during heating or cooling and a combination of introducing one or more particles into the substance at the same time intervals can interrogate the viscosity, density, and thermal perturbation response. In some embodiments, the perturbation can comprise all three perturbations. One such example is loading the fluidic chamber horizontally with particles loaded into the upmost sections of the channel and then simultaneously pivoting the fluidic chip upright into a thermal perturbation substance.

Optical Sensor

For some system embodiments, an optical sensor can be used to capture the response of the substance. The optical image sensor can be any sensor known in the art for recording digital images, such as a charge coupled devices (CCD), complementary metal-oxide-semiconductors (CMOS), or other image detecting sensors. In some embodiments, the optical image sensor can comprise a digital camera. In some systems, the position of the fluidic chip and the optical sensor are conserved such that each time a measurement is taken the relative position of the fluidic chip and the optical sensor are the same for each measurement.

Controller

A controller can include multiple engines for performing the processes and functions described herein. The engines can include programmed instructions for performing processes as discussed herein substance identification. The programming instructions can be stored in a memory. The programming instructions can be implemented in C, C++, JAVA, or any other suitable programming languages. In some embodiments, some or all of the portions of the controller including the engines can be implemented in application specific circuitry such as ASICs and FPGAs. Some aspects of the functionality of the controller can be executed remotely on a server over a network. The functionality of the engines is not necessarily required to be separated.

The controller can include a signal collection engine. The signal collection engine can enable acquisition of raw data from sensors embedded in a substance identification system.

In some embodiments, the signal collection engine can also perform signal preprocessing on the raw data. Signal preprocessing can include noise filtering, smoothing, averaging, and other signal preprocessing techniques to clean the raw data. In some embodiments, portions of the signals can be discarded by the signal collection engine.

The controller can also include a feature extraction engine. The feature extraction engine can extract relevant features from the signals collected by the signal collection engine. The features can be in time domain and/or frequency domain. For example, some of the features can include amplitude, bandwidth, area under the curve (e.g., power), energy in frequency bins, peak frequency, ratio between frequency bands, and the like. The features can be extracted using signal processing techniques such as Fourier transform, band pass filtering, low pass filtering, high pass filtering and the like.

The controller can further include a rule generation engine. The rule generation engine can use the extracted features from the collected signals and determine rules that correspond to substance identification. The rule generation engine can automatically determine a correlation between specific extracted features and substance identification.

In some embodiments, the rule generation engine relies on calibration instructions to determine rules between features and outcomes. The rule generation engine can employ machine learning modeling along with signal processing techniques to determine rules, where machine learning modeling and signal processing techniques include but are not limited to: supervised and unsupervised algorithms for regression and classification. Specific classes of algorithms include, for example, Artificial Neural Networks (Perceptron, Back-Propagation, Convolutional Neural Networks, Recurrent Neural networks, Long Short-Term Memory Networks, Deep Belief Networks), Bayesian (Naive Bayes, Multinomial Bayes and Bayesian Networks), clustering (k-means, Expectation Maximization and Hierarchical Clustering), ensemble methods (Classification and Regression Tree variants and Boosting), instance-based (k-Nearest Neighbor, Self-Organizing Maps and Support Vector Machines), regularization (Elastic Net, Ridge Regression and Least Absolute Shrinkage Selection Operator), and dimensionality reduction (Principal Component Analysis variants, Multidimensional Scaling, Discriminant Analysis variants and Factor Analysis). In some embodiments, the controller can use the rules to automatically determine outcomes. The controller can also use the rules to control or change settings of the substance identification system. Accordingly, the rules can improve operation of the substance identification system. The generated rules can be saved in a memory medium.

Image Processor

Some substance identification systems can comprise a processor for a processor for producing a chronological fingerprint from the captured response of the substance and comparing the chronological fingerprint of the substance to chronological fingerprints of known substances to identify the substance, where the chronological fingerprint is a multi-dimensional digital image of the response of the substance to the perturbation as a function of time. In some systems, the processor can compare chronological fingerprints from the substance and substances concurrently measured in the same experiment, whether known, unknown, or both known and unknown. In some embodiments, the processor can compare chronological fingerprints from the substance with chronological fingerprints stored in a database. Some processors can compare the chronological fingerprint from the substance to both stored chronological fingerprints and concurrently measured chronological fingerprints of known substances. In some embodiments, image processing and analysis software known in the art can be used to compare chronological fingerprints to determine to identify the substance.

In some embodiments, the system can further comprise non-volatile memory for holding a database of stored chronological fingerprints for known substances. The database of chronoprints may be hosted on an online server, wherein the processor can access such an online server for chronoprint comparisons. For some systems, the processor can retrieve the stored chronological fingerprints and then compare them using image analysis software to the measured chronological fingerprints.

Computer Implemented Method for Identifying a Substance

Another embodiment can describe a computer program product comprising a non-transitory computer usable medium having computer readable code embodied therein for identifying a substance, which comprises the steps of: (1) obtaining one or more time-dependent perturbations of one or more substances; (2) producing a chronological fingerprint of the sample experiencing the perturbation, where the chronological fingerprint is a multi-dimensional digital image of the response of the sample as a function of time; and (3) comparing the chronological fingerprint of the sample measured to chronological fingerprints of one or more known samples, each sample measured either in the same experiment or from a database of chronological fingerprints, to determine the substance being measured.

Some computer-readable code can further comprise the step of converting the chronological fingerprint to a binary chronological fingerprint (a computer "hash" of the original chronological fingerprint) before comparing. Some computer-readable code can further comprise the step of tracing the features of the binary chronological fingerprint before comparing, where the comparing is done on the traced features. Some computer readable-code can further comprise the step of calculating the sum of the pixel-by-pixel differences between two chronological fingerprints.

EXAMPLES

It has been discovered that the methods and systems described herein can provide the ability to distinguish between chemically different samples from observing their responses to perturbations. These benefits are further demonstrated by the following examples, which are intended to be illustrative of the embodiments of the disclosure but are not intended to limit the scope or underlying principles in any way. Specifically, to demonstrate the versatility of the methods and systems it is shown by way of example that the embodiments can distinguish between authentic and adulterated foodstuffs, identify adulterated or counterfeit medication, and distinguish between toxic and nontoxic pharmaceutical ingredients.

Example 1.1: Fabricating of Fluidic Chips

The micro-fluidic chips were designed in Adobe Illustrator (Adobe Systems Inc., San Jose, CA). Each fluidic chip was 125 mm long and 25 mm wide and contained six plena, or parallel microfluidic channels. Each channel was 1.5 mm wide, 0.5 mm deep, and 115 mm long, with 2.5 mm diameter input/output reservoirs at each end, 1.5 mm space between channels, and markers spaced every 1 mm along the sides of the chip for length measurements. The chip design was engraved into 3 mm thick poly(methylmethacrylate) pieces (Professional Plastics Inc., Fullerton, CA) using a computer-controlled hobbyist-grade milling machine (Bantam Tools, Berkeley, CA). The open channels were then enclosed/plugged by applying PCR tape (Bio-Rad Laboratories, Hercules, CA) to the chip.

Example 1.2: Preparation of Samples

Several different types of liquid samples were prepared. For the application of the method to the problem of counterfeit food products, samples of two pure food oils were used: extra virgin olive oil (Wal-Mart Stores Inc., Bentonville, AR, USA) and unrefined peanut oil (Spectrum Organic Products, Petaluma, CA, USA). In addition, a 1:1 (vol/vol) mixture of the pure two oils was also created to serve as an adulterated oil sample.

To explore the ability of the method to determine the authenticity of medications, six different lots of NyQuil Severe Cold and Flu medicine were acquired. NyQuil is a liquid medication containing acetaminophen, phenylephrine, doxylamine succinate, dextromethorphan, and glycerol. The drugs had expiration dates spanning a four-month period from July to October 2019. Additionally, to simulate the detection of an adulterated medicine, diluted or watered down, 50%, 75%, 90%, and 95% (vol/vol) dilutions of NyQuil Severe Cold and Flu medicine in water were created.

Finally, to show the applicability of the method to distinguishing two occasionally confused chemicals in pharmaceutical manufacturing, samples of diethylene glycol (Sigma-Aldrich, St. Louis, MO, USA), a transparent and sweet-tasting but poisonous liquid, and glycerol (Aldrich), a similar but nonpoisonous liquid, were obtained.

About 75 µL of each sample was then loaded into the fluidic chips for each experiment.

Example 2.1 Obtaining Response Measurements (Chronological Fingerprints)

Once a fluidic chip was filled with samples to analyze, as shown in FIG. 2 (B), one end of the chip was partially submerged in a liquid nitrogen bath while recording a video of the chip contents using an inexpensive USB microscope (FIG. 2 (A); Monoprice, Rancho Cucamonga, CA) to initiate a thermal perturbation. It was observed that the perturbation created a dynamic temperature gradient that quickly cooled the lower regions of the fluidic chip, and then slowly cooled the rest of the chip over the next few seconds. All six sample channels in the chip were exposed to the same dynamic temperature gradient. After about 80 seconds for the oil samples and 160 seconds for the cold medicine samples, no further changes were observed, and the video recording was then ended, see FIG. 2 (C). A custom MATLAB script was then executed on a processor to convert each video into six chronological fingerprints, one per sample. For each sample, the script extracted an image of the entire plenum, or fluidic channel, from each frame of the video, see FIG. 2 (D). The script then averaged each row of pixels in each channel image to convert it to a single column of pixels. By then placing all of these columns of pixels side-by-side, the script creates a bitmap image that is the sample's chronological fingerprint, with space, or distance along the channel, in the vertical dimension and time in the horizontal dimension, see FIG. 1 (E). This process was then repeated for each sample in the experiment, and the resulting chronological fingerprints were ready for comparison and similarity analysis.

Example 2.2 Comparing Chronological Fingerprints

In the experiments, the chronological fingerprints are bitmap images so they could be compared using a variety of different techniques, including image similarity algorithms developed by computer scientists. Although many more techniques are available in the art, three different techniques were used to compare chronological fingerprints: feature tracing, image differences, and image hashing.

Example 2.3 Comparing Chronological Fingerprints Using Feature Tracing

Figure 3:
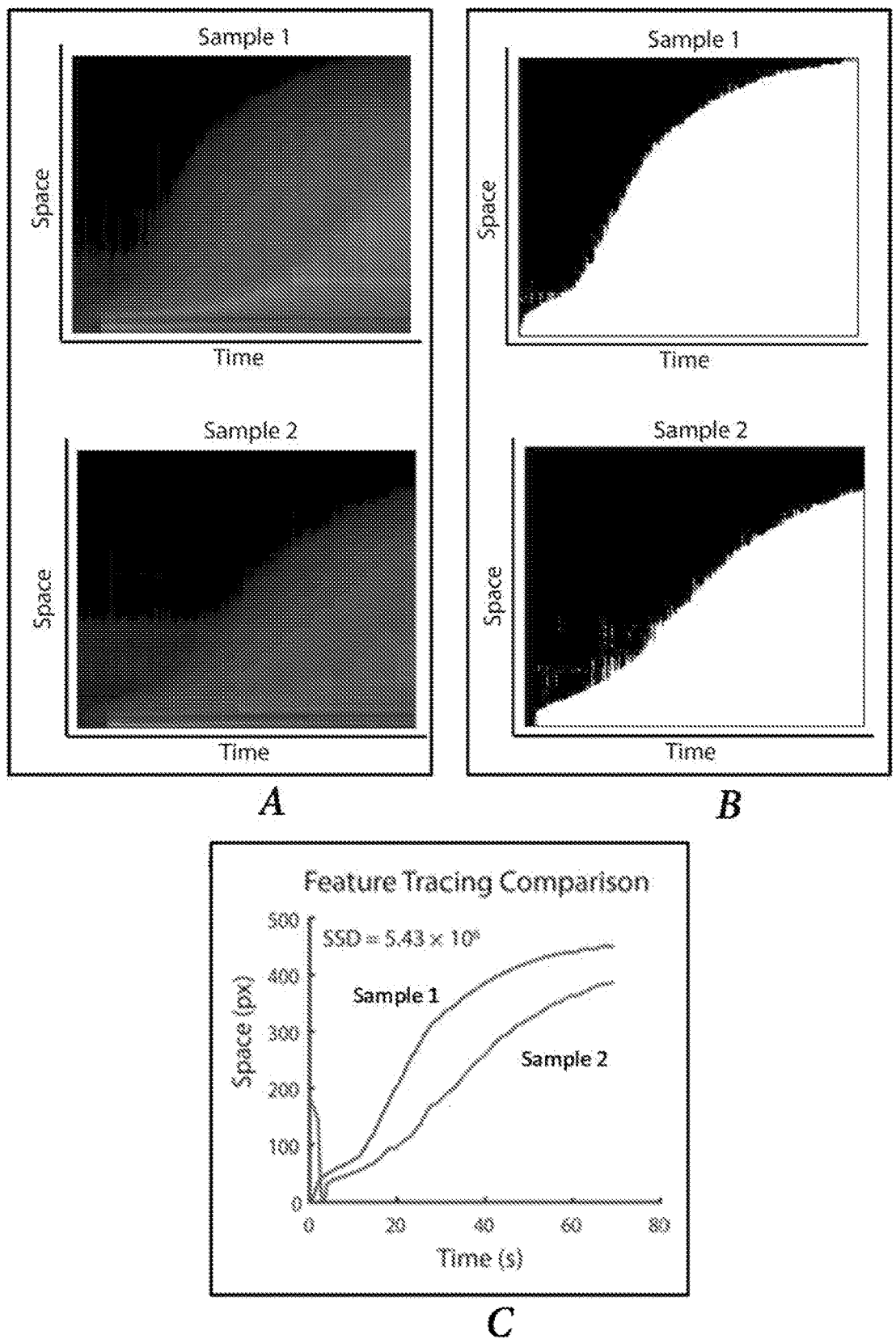
FIG. 3. Overview of the feature tracing method of comparing chronological fingerprints (in this case, obtained from two different food oils). Monochrome chronological fingerprints of each sample (A) are converted to binary chronological fingerprints (B) by comparing each pixel value to a constant threshold value; pixels above the threshold are colored white, and pixels below the threshold are colored black. The code within the processor then traces the boundary between white and black pixels on each binary chronological fingerprint, and the resulting traces are smoothed slightly and plotted together to compare the two chronological fingerprints (C). Traces that are significantly different (like these) confirm that the two samples are chemically different. The sum of squared differences (SSD) between the y-axis values of the curves at each point along the curves ($5.43\times10^6$ in this case) serves to quantify the degree of similarity between the two samples of food oils.

For simpler chronological fingerprints with just one or two dominant features, feature tracing is a viable option. Feature tracing is when boundary between these features are traced and each chronological fingerprint can be converted to a curve; these curves can then be compared to each other to quantify the similarity of the samples. An example of this feature tracing approach for chronological fingerprint comparison is shown in FIGS. 3 (A-C). In this process, a custom MATLAB program first enhances contrast by taking the pixel values of the first frame, or the first column of pixels in the chronological fingerprint, halving these values, and subtracting the result from each remaining column of pixels in the chronological fingerprint. This process helps remove background noise that affects each frame of the movie and the chronological fingerprints. The program then converts each chronological fingerprint from color to monochrome, with the monochrome shown in FIG. 3 (A), then the program compares the value of each pixel to a constant threshold provided by the user; pixels with values below the threshold are colored solid black, and pixels with values above the threshold are colored solid white, to create a binary chronological fingerprint as shown in FIG. 3 (B). The program then traces the boundary between the black and white pixels and converts this trace into a curve as depicted in FIG. 3 (C). Rarely, a column of pixels is encountered where the program fails to find the interface between the black and white pixels; in these cases, the program reuses the last successful interface location from the previous column of pixels. Finally, the curve is smoothed slightly using a Savitzky-Golay filter (3rd order polynomial; 31-point full window width). See Savitzky, A. et al., Smoothing and differentiation of data by simplified least squares procedures., 36 Anal. Chem. 1627-1639 (1964); Steinier, J. et al., Smoothing and differentiation of data by simplified least square procedure., 44 Anal. Chem. 1906-1909 (1972). If the two curves are similar, this suggests that the two samples analyzed may be the same; but if the two curves are significantly different, this is proof that the samples are chemically different. The degree of similarity between two samples is quantified by summing the squared differences between the y-axis values of the curves (the distances along the channel) at each point along the curves.

Example 2.4 Comparing Chronological Fingerprints Using Image Differences

Figure 4:
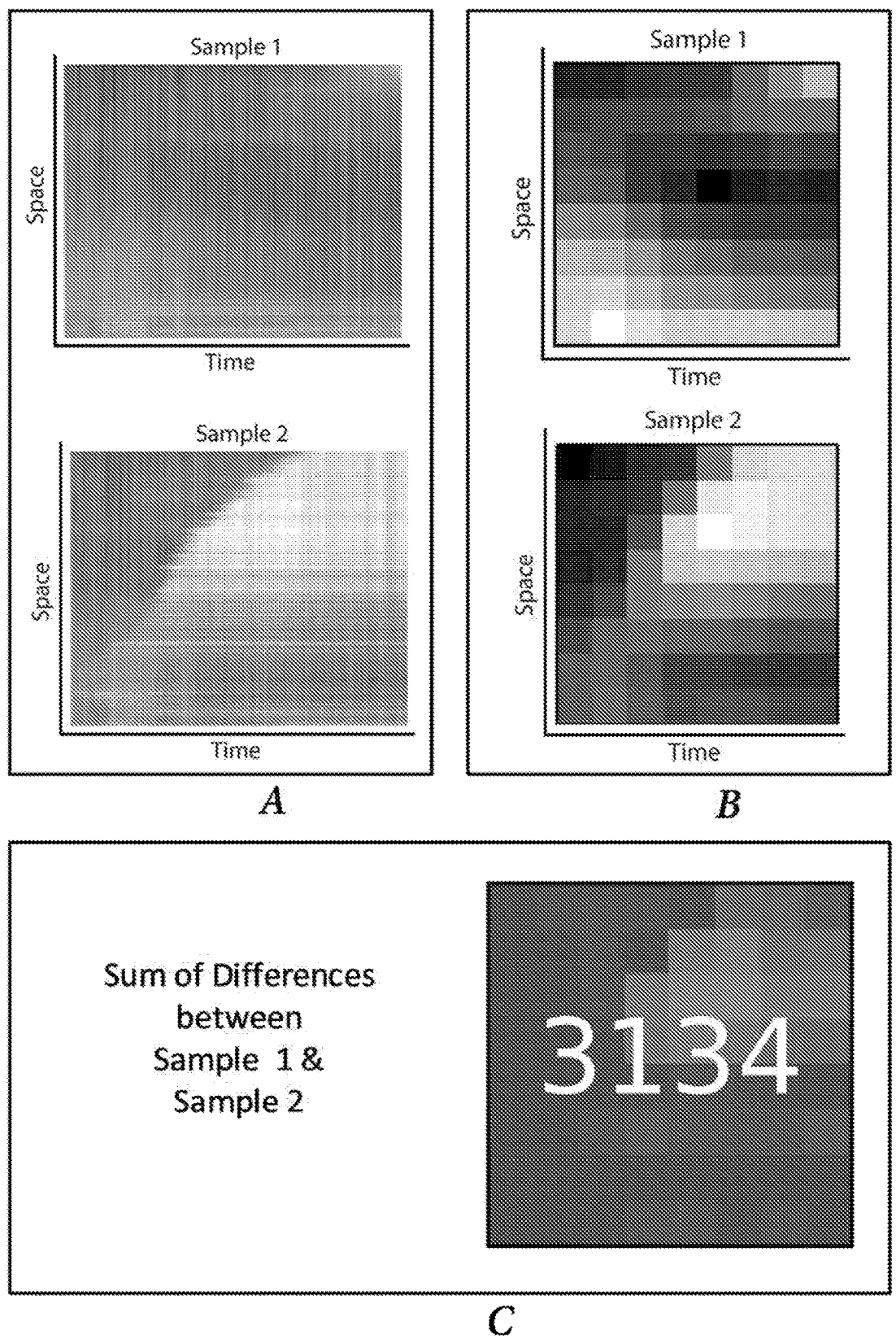
FIG. 4. Overview of the image differences method of comparing chronological fingerprints (in this case, obtained from authentic and diluted samples of liquid cold medicine). Chronological fingerprints of each sample (A) are converted to reduced-resolution (8×8 pixel) monochrome chronological fingerprints (B). The monochrome chronological fingerprints are then compared by calculating the difference between the pixel values at each location; the resulting image (C) shows which regions of the chronological fingerprints are similar (blue) and which are different (red). The sum of these pixel difference values (3134 in this example) quantifies the similarity of these chronological fingerprints on a scale from 0 (completely identical) to 16320 (completely different). In practice, it was found that a threshold of about 1500 generally separates the image differences scores of identical substances from different substances, so the image differences score of 3134 in this example is significantly greater than 1500 and confirms that these two samples of cold medicine are chemically different.

While the feature tracing method described above works well for simpler chronological fingerprints, more complex chronological fingerprints cannot be easily reduced to simple curves for comparison. For these chronological fingerprints, the digital images are compared directly. The image differences method for chronological fingerprint comparison calculates the sum of the pixel-by-pixel differences between reduced-resolution versions of two chronological fingerprints. An example of using the image differences process is shown in FIGS. 4 (A-C). In this process, each chronological fingerprint, FIG. 4 (A), is first converted from color to monochrome, then the spatial resolution of each chronological fingerprint is down sampled to 8 by 8 pixels, see FIG. 4 (B). Each of the chronological fingerprint's 64 pixels then has a value between 0 (black) and $2^8-1=255$ (white). To compare two chronological fingerprints, the absolute value of the difference between the pixel values at each pixel location is calculated, and the sum of these values represents the image difference score for the two images, see FIG. 4 (C). An image difference score of 0 indicates that the two chronological fingerprints are exactly identical. The highest possible image difference score, $(2^8-1)$ 64=16,320, corresponds to comparing an all-white chronological fingerprint with an all-black chronological fingerprint. In practice, it was found that a threshold of about 1500 separated most sample pairs that are identical, an image difference score <1500, from sample pairs that were different, an image difference score >1500.

Example 2.5 Comparing Chronological Fingerprints Using Image Hashing

Figure 5:
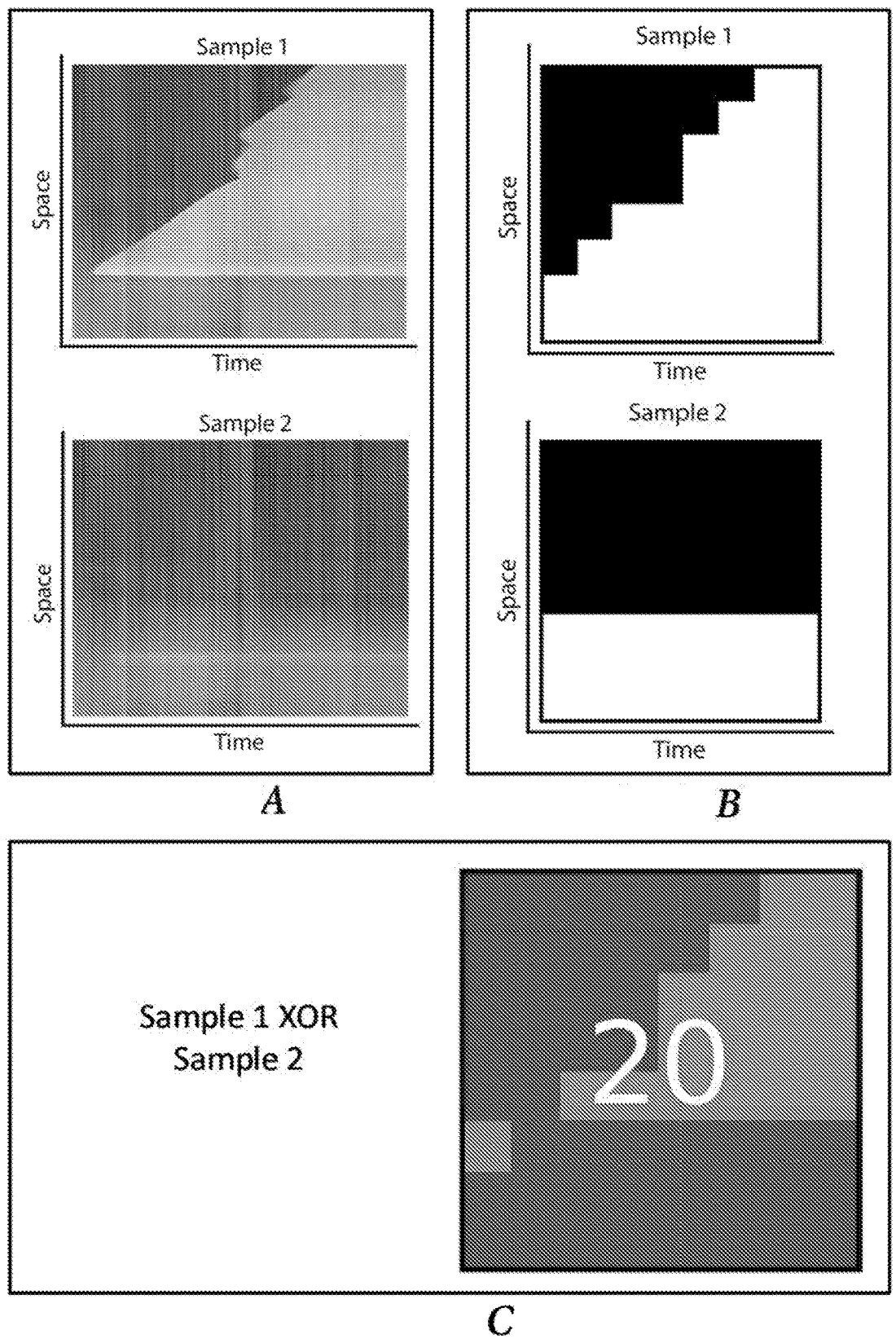
FIG. 5. Overview of the image hashing method of comparing chronological fingerprints (in this case, obtained from authentic and diluted samples of liquid cold medicine). Chronological fingerprints of each sample (A) are converted to reduced-resolution (8×8 pixel) binary chronological fingerprints (B) by comparing each pixel value to a constant threshold. The binary chronological fingerprints are then compared by computing the exclusive OR (XOR) of the pixels at each location in the binary chronological fingerprints, interpreting black=binary "0" or FALSE and white=binary "1" or TRUE. The resulting XOR image (C) is shown with blue pixels wherever the chronological fingerprints are similar and red pixels wherever the chronological fingerprints are different. The number of red pixels in the XOR image, the image hashing score (20 in this example), quantifies the degree of similarity of these chronological fingerprints on a scale from 0 (completely identical) to 64 (completely different). In practice, we found that XOR images with more than about 10 red pixels corresponded to chronological fingerprint pairs from different samples, so the image hashing similarity score of 20 in this example confirms that these two samples of cold medicine are chemically different.

The third chronological fingerprint comparison method used, image hashing, is shown in FIG. 5 (A-C). This method converts each chronological fingerprint to a reduced-size binary representation, or a "hash," that can then be compared to other chronological fingerprints' hashes. The process starts by using the 8-by-8 pixel, monochrome version of the chronological fingerprints created in the image differences method above. Then, each pixel is converted to either solid white or solid black depending on whether its value lies above or below a threshold, see FIG. 5 (B). Four different values for this threshold were explored:
  Local Mean: the average pixel value in each chronological fingerprint was used as the threshold.
  Local Median: the median pixel value in each chronological fingerprint was used as the threshold.
  Global Mean: the average pixel value across all six chronological fingerprints in an experiment was used as the threshold.
  Global Median: the median pixel value across all six chronological fingerprints in an experiment was used as the threshold.

Once a chronological fingerprint was converted to an 8 by 8 binary image, it has effectively been reduced to a 64-bit "hash" of the original chronological fingerprint. To calculate the similarity between two image hashes, the software in the processor then interpreted the white pixels as binary "1" or TRUE and the black pixels as "0" or FALSE, and then calculated the exclusive OR, or XOR, of each pixel pair between the images. If two pixels in the same location in two image hashes were the same, that is, they were both white or both black, then the result of the XOR of the pixel values is always 0 (e.g., 0 XOR 0=0 and 1 XOR 1=0). However, if the two pixels were different, such as if one was black and the other was white), then the result of the XOR of the pixel values is always 1 (that is, 1 XOR 0=1 and 0 XOR 1=1). By then adding up the sum of all 64 pixel-wise XOR operations, two chronological fingerprints' image hashing similarity score can be obtained, see FIG. 5 ©. This value ranges from 0 for two chronological fingerprints with identical image hashes to 64 for chronological fingerprints with exactly opposite image hashes.

Example 3.1 Case Study—Detecting Food Fraud

Figure 6:
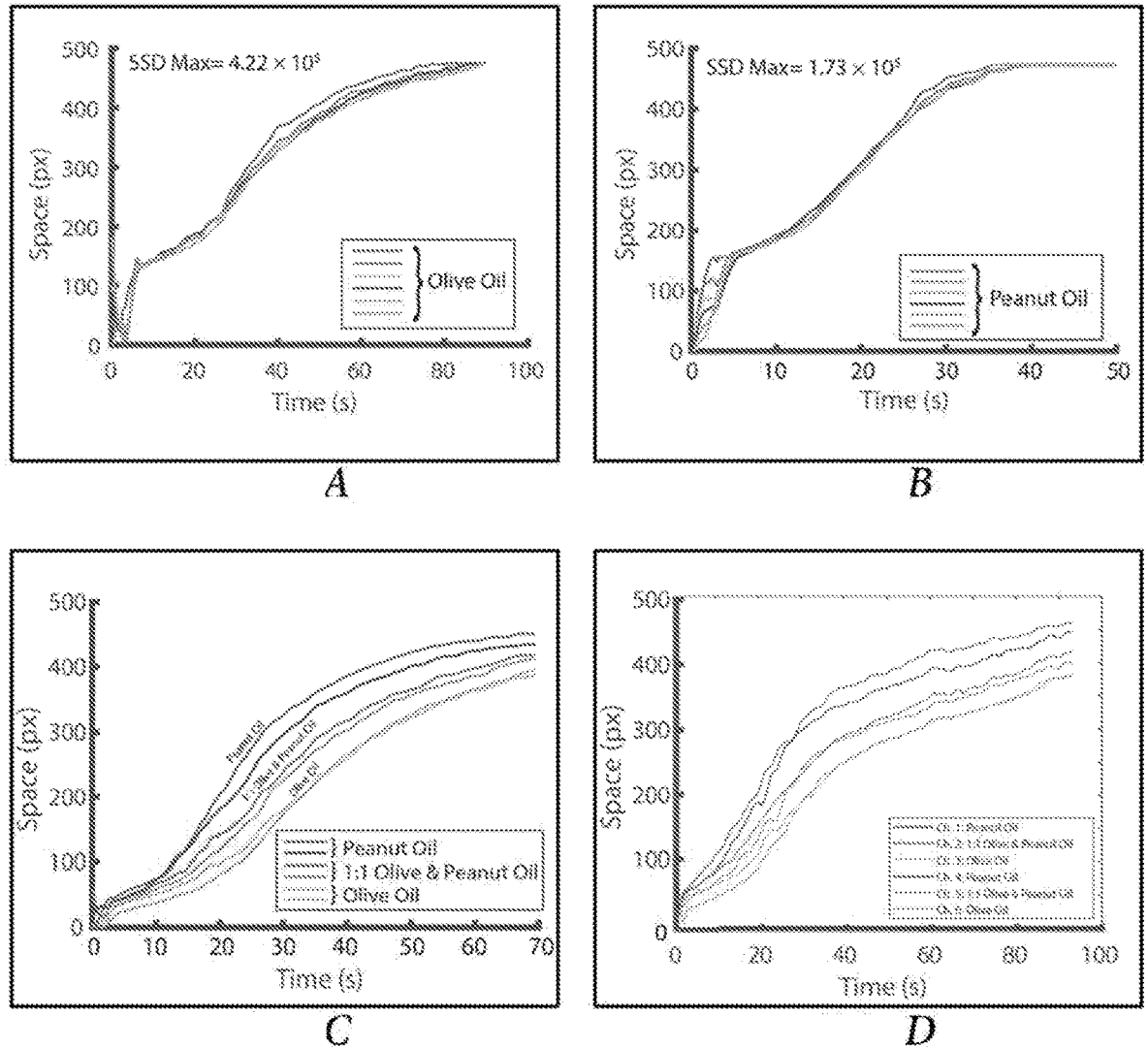
FIG. 6. Identifying authentic and adulterated food oils using chronological fingerprints. Each plot compares chronological fingerprints from six food oil samples, converted to curves using the feature tracing method. (A) Chronological fingerprint curves from six identical samples of olive oil are nearly identical and differ by a sum of squared differences (SSD) that is $4.22 \times 10^5$ or less; this is less than the experimentally observed threshold of $1 \times 10^6$ and confirms that the oil samples are identical. (B) Chronological fingerprint curves from six identical samples of peanut oil are similarly identical. (C) Chronological fingerprint curves from two samples each of three different oils (olive oil, peanut oil, and a 1:1 mixture of olive and peanut oil) are similar within each oil type but significantly different between the different oil types. The maximum sum of squared differences between two different oil types ($5.77 \times 10^6$ difference between the olive oil and peanut oil samples) is greater than the threshold of $1 \times 10^6$ and confirms that these oils are different. (D) This is a replication of the main experiment in FIG. 6C. Among the samples of the same oil types, the chronological fingerprint traces had relatively small differences: the maximum sum-of-squared-differences of $8.47 \times 10^4$, $3.61 \times 10^5$, and $1.35 \times 10^5$ between the two 100% olive oil samples, the two 100% peanut oil samples, and the two 1:1 olive and peanut oil samples, respectively. However, between the different oil types, the chronological fingerprint traces had greater differences: the maximum sum-of-squared-differences were $7.34 \times 10^6$ between the 100% olive oil and 100% peanut oil samples.

To determine if chronological fingerprints can be used to identify adulterated food oils, the technique was used to analyze various samples of pure oils and oil mixtures. Since these samples resulted in relatively simple chronological fingerprints, the feature tracing comparison technique was used to convert each chronological fingerprint into a curve and quantify sample similarity. To start a fluidic chip was loaded with six identical samples of 100% extra virgin olive oil before partially submerging the chip in liquid nitrogen, recording a video of the chip as it cools, and converting the video into six chronological fingerprints. The results from performing feature tracing analysis on each chronological fingerprint are shown in FIG. 6 (A). Since all six samples were identical, we expected the resulting curves to be very similar, and this is indeed the case. The maximum sum of squared differences between the curves, $4.22 \times 10^5$, is relatively low and indicates that the samples are likely identical. In another experiment, we analyzed six identical samples of 100% unrefined peanut oil. As expected, the resulting curves were again nearly identical within each sample, as shown in FIG. 6(B), with a maximum sum of squared difference of $1.73 \times 10^5$. These results support the claim that all six samples in the fluidic chip received the same perturbation, and if the samples are identical, then the resulting chronological fingerprints will be very similar, with sum of squared differences between their feature tracing curves less than about $1 \times 10^6$.

To determine whether different samples produce different chronological fingerprints in the same experiment, two samples from three different oils were each loaded into a fluidic chip. Channels 1 and 4 contained pure peanut oil, channels 3 and 6 contained pure olive oil, and channels 2 and 5 contained a 1:1 (vol/vol) mixture of olive and peanut oil. Chronological fingerprints were then obtained for each sample and analyzed using the feature tracing method; the resulting curves are shown in FIG. 6 (C), repeated results are also presented in FIG. 6 (D). Within each oil type, each pair of samples resulted in very similar curves: the sum of squared differences was only $5.98 \times 10^4$ for the two olive oil samples, $2.55 \times 10^5$ for the two peanut oil samples, and $1.04 \times 10^5$ for the two olive/peanut mixture samples. However, different oil types had very different curves: the maximum sum of squared differences was $5.77 \times 10^6$ for the olive oil and peanut oil samples. In this and other experiments, we found that chronological fingerprints with feature tracing scores greater than about $1 \times 10^6$ indicated that the oils were different, and chronological fingerprints with scores less than $1 \times 10^6$ indicated that the oils were the same.

Example 3.2 Case Study—Detecting Counterfeit Medicine

Figure 7:
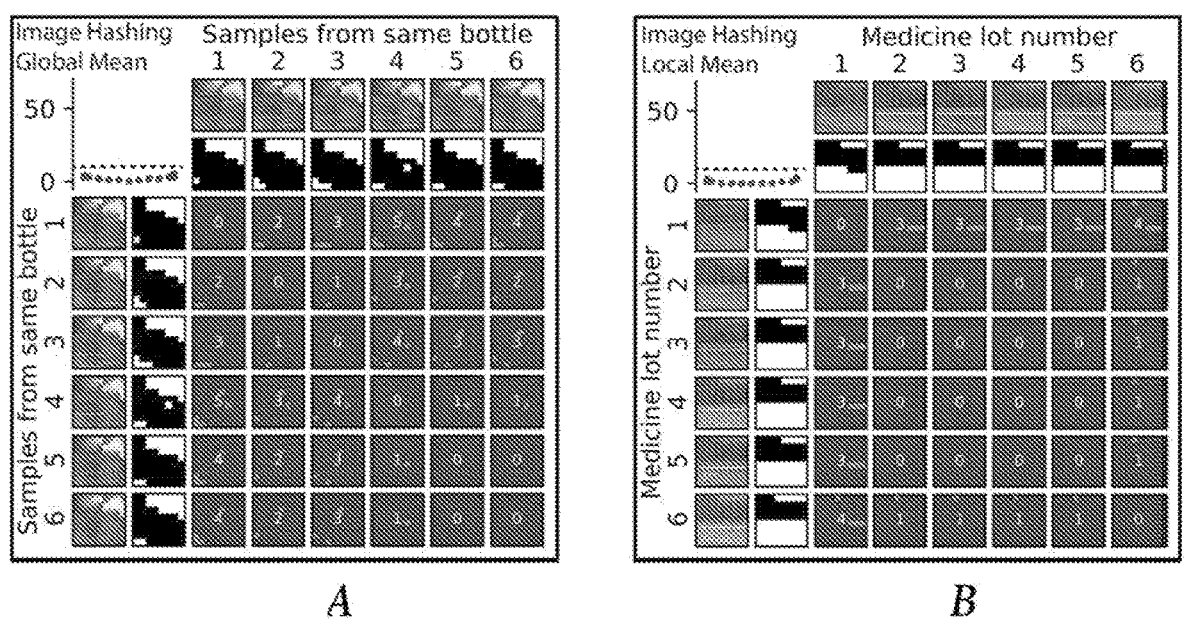
FIG. 7. Detecting authentic liquid cold medicine using chronological fingerprints. Each set of images shows six chronological fingerprints along with all pairwise comparisons of the six samples in each experiment, plus a small summary plot of difference scores (blue points=known identical samples). (A) Chronological fingerprints from six identical samples of cold medicine from the same bottle, compared using the image hashing method with the global mean pixel value used as the threshold. The resulting image hashes never differ by more than 5 bits; this is well below the 10-bit experimentally observed threshold between identical and different samples (dotted line in summary plot) and confirms that all six medicine samples are identical. (B) Chronological fingerprints from six samples of cold medicine from six different manufacturer's lot numbers, compared using the image hashing method with the local mean pixel value used as the threshold. The resulting image hashes never differ by more than 4 bits; this again confirms that the medicine samples are identical (despite having manufacture dates spanning a four-month period). (C-G) Comparison of different chronological fingerprint similarity algorithms for six cold medicine samples from one bottle, same experiment as in FIG. 7 (A). (H-L) Comparison of different chronological fingerprint similarity algorithms for six cold medicine samples from six different lots, same experiment as in FIG. 7 (B).
Figure 7:
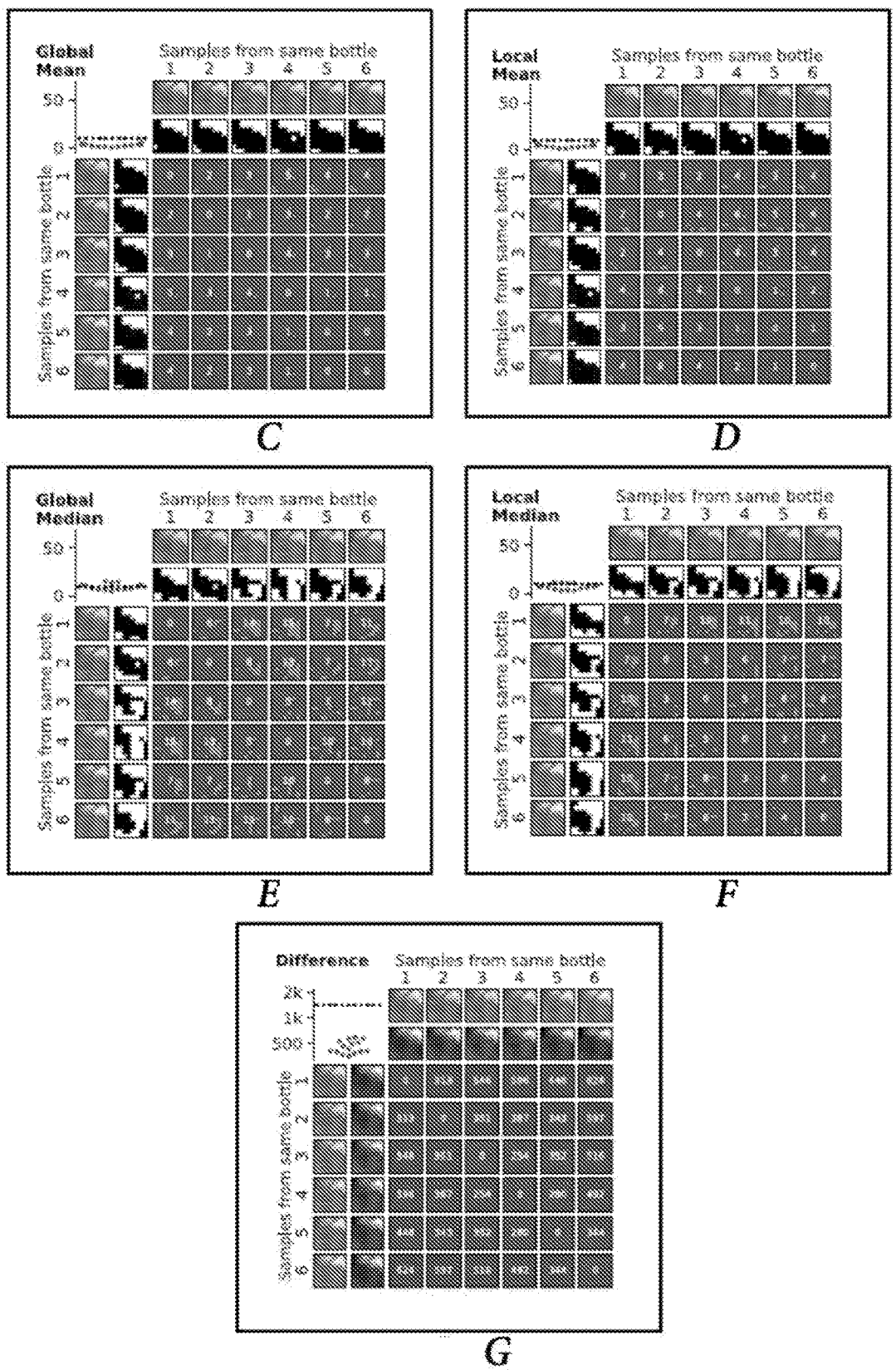
Figure 7:
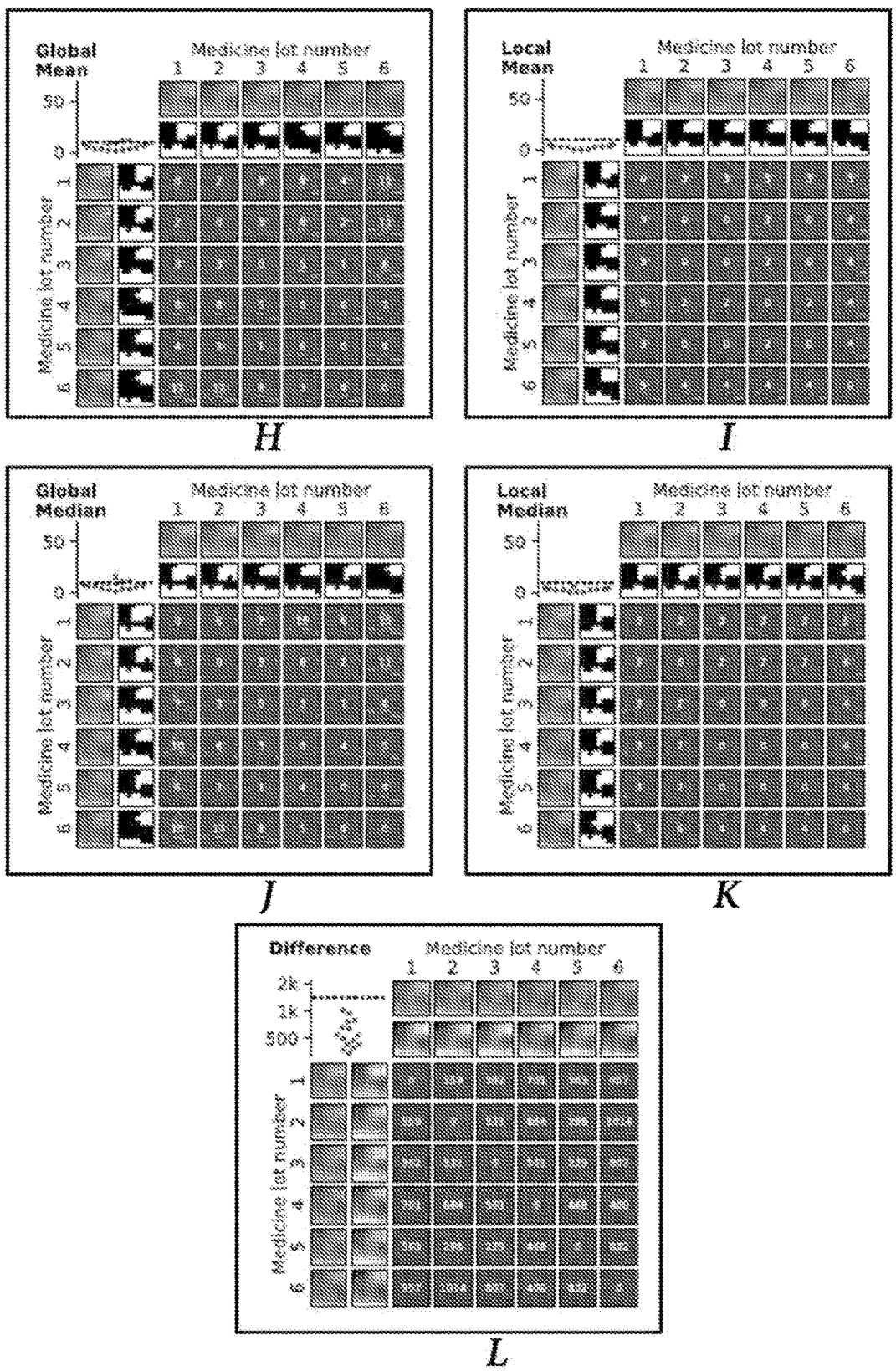

To test the use of chronological fingerprints for distinguishing authentic and adulterated medicine samples, the method and system was used to analyze samples of over-the-counter cold medicine. These samples resulted in complex chronological fingerprints, so image differences and image hashing techniques were used to compare the chronological fingerprints. First, a fluidic chip was filled with six samples of cold medicine from the same bottle and a chronological fingerprint obtained for each sample. Since the drug samples were identical, the experimental results, FIG. 7 (A), confirmed the expectation that the chronological fingerprints would be similar: using image hashing with a global mean pixel value as the threshold, all six chronological fingerprints' hashes differed by only 5 or fewer bits out of 64. This small difference in the chronological fingerprints' image hashes confirmed that the cold medicine samples were identical. We then filled the chip with six samples of cold medicine from six different medicine manufacturers' lots and obtained a chronological fingerprint for each sample. Since these medicine samples are all the same brand, it was expected that the resulting chronological fingerprints would also be very similar. The experimental results, shown in FIG. 7 (B) also confirmed this expectation: using image hashing with a local mean pixel value as the threshold, all six chronological fingerprints' hashes differed by only 4 or fewer bits out of 64. This small difference in the chronological fingerprints' image hashes confirmed that these cold medicine samples are also identical, despite being manufactured at different times over a 4-month period. Additional chronological fingerprint experiments, as well as the different analysis methods for the experiments shown in FIG. 7 (C-L).

Next, the chronological fingerprints for samples of adulterated medicine, by diluting it with water, were measured to see if the method can be used as a basis of a test to detect adulterated medicines. A fluidic chip with two samples each of 50%, 75% and 100% (vol/vol) dilutions of cold medicine in water. Then the experiment was then run. The resulting chronological fingerprints were then analyzed using image hashing with a global mean pixel value as the threshold. The results, shown in FIG. 8 (A-B), show that within each dilution, the two samples' chronological fingerprints are identical, or nearly so: the two samples of 100% medicine have identical image hashes, as do the two samples of 75% medicine, and the two samples of 50% medicine differ by only 4 bits. However, between the different dilutions, the samples' chronological fingerprints were very different: the 100% and 75% dilutions differed by 24 bits, the 75% and 50% dilutions differed by 23 and 27 bits, and the 100% and 50% dilutions differed by 47 and 51 bits. In general, it was found that if the chronological fingerprint image hashes differed by more than about 10 bits, it indicated that the medicines were different (and potentially adulterated), and if hashes that differed by less than 10 bits, it usually indicated that the medicines were the same. Additional chronological fingerprint experiments for the 50%, 75%, and 100% (vol/vol) dilutions of cough medicine in water, as well as the different analysis methods for the experiment shown in FIG. 8 (C-Q), are provided in Supporting Information.

Figure 8:
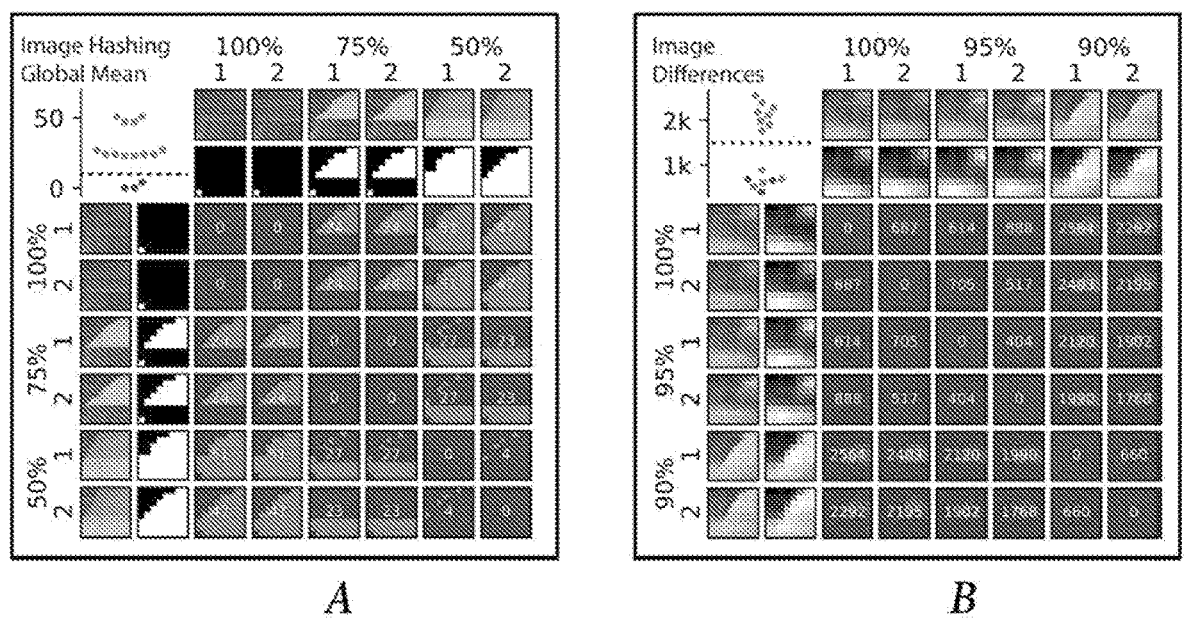
FIG. 8. Detecting adulterated liquid cold medicine using a chronological fingerprint. (A) Chronological fingerprint from two samples each of three different dilutions of cold medicine in water (50%, 75%, and 100%) again compared using the image hashing method. The resulting image hashes successfully confirm that the two samples of each dilution are identical (difference scores of 0, 0, and 4 bits; all <10), and all samples of different dilutions are different (difference scores from 23 to 51 bits; all >10). (B) Chronological fingerprints from two samples each of three additional dilutions of cold medicine (90%, 95%, and 100%) were compared using the image differences method. The resulting difference images successfully distinguished the 90% samples from the 95% and 100%, with difference scores from 1768 to 2564 (all >1500, the experimentally observed threshold between identical and different samples marked with the dotted line). However, the images failed to distinguish the 100% and 95% samples, with difference scores from 517 to 888 (all <1500 and therefore erroneously identified as identical; red points below the dotted line). Thus, chronological fingerprints are capable of identifying samples of this cold medicine that have been diluted by as little as 10%. (C-G) Comparisons of different chronological fingerprint similarity algorithms for 50%, 75%, and 100% (vol/vol) dilutions of cold medicine in water, same experiment as in FIG. 8 (A). (H-L) Replicate of the analysis of 50%, 75%, and 100% cold medicine samples, the experiment shown in FIG. 8 (A). All three dilutions types are distinguishable. The global median image hashing analysis performed best for this experiment, with a maximum pixel difference of 28 of 64 pixels between the 75% and 100% sample chronological fingerprints. (M-Q) Replicate of the analysis of 50%, 75%, and 100% cold medicine samples, same experiment as in FIG. 8 (A). All three sample types are distinguishable. The local median image hashing analysis performed the best for this experiment, with a maximum pixel difference of 28 out of 64 pixels between the 75% and 100% sample chronological fingerprints. (R-V) Comparisons of different chronological fingerprint similarity algorithms for 90%, 95%, and 100% (vol/vol) dilutions of cold medicine in water, same experiment as in FIG. 8 (B). (W-AA) Replicate of the analysis of 90%, 95%, and 100% cold medicine samples, same experiment as in FIG. 8 (B). The 90% cold medicine samples are distinguishable from the others, but the 95% and 100% samples were not distinguishable. The local median image hashing analysis performed the best for this experiment, with a maximum pixel difference of 26 out of 64 pixels between the 90% and 100% sample chronological fingerprints. (AB-AF) Replicate of the analysis of 90%, 95%, and 100% cold medicine samples, replicate of experiment in FIG. 8 (B). The 90% cough medicine sample is distinguishable from the others, but the 95% and 100% samples were not distinguishable. The image differences analysis performed the best for this experiment, with a maximum sum of pixel difference of 3134 out of 16320 between the 90% and 100% sample chronological fingerprints.
Figure 8:
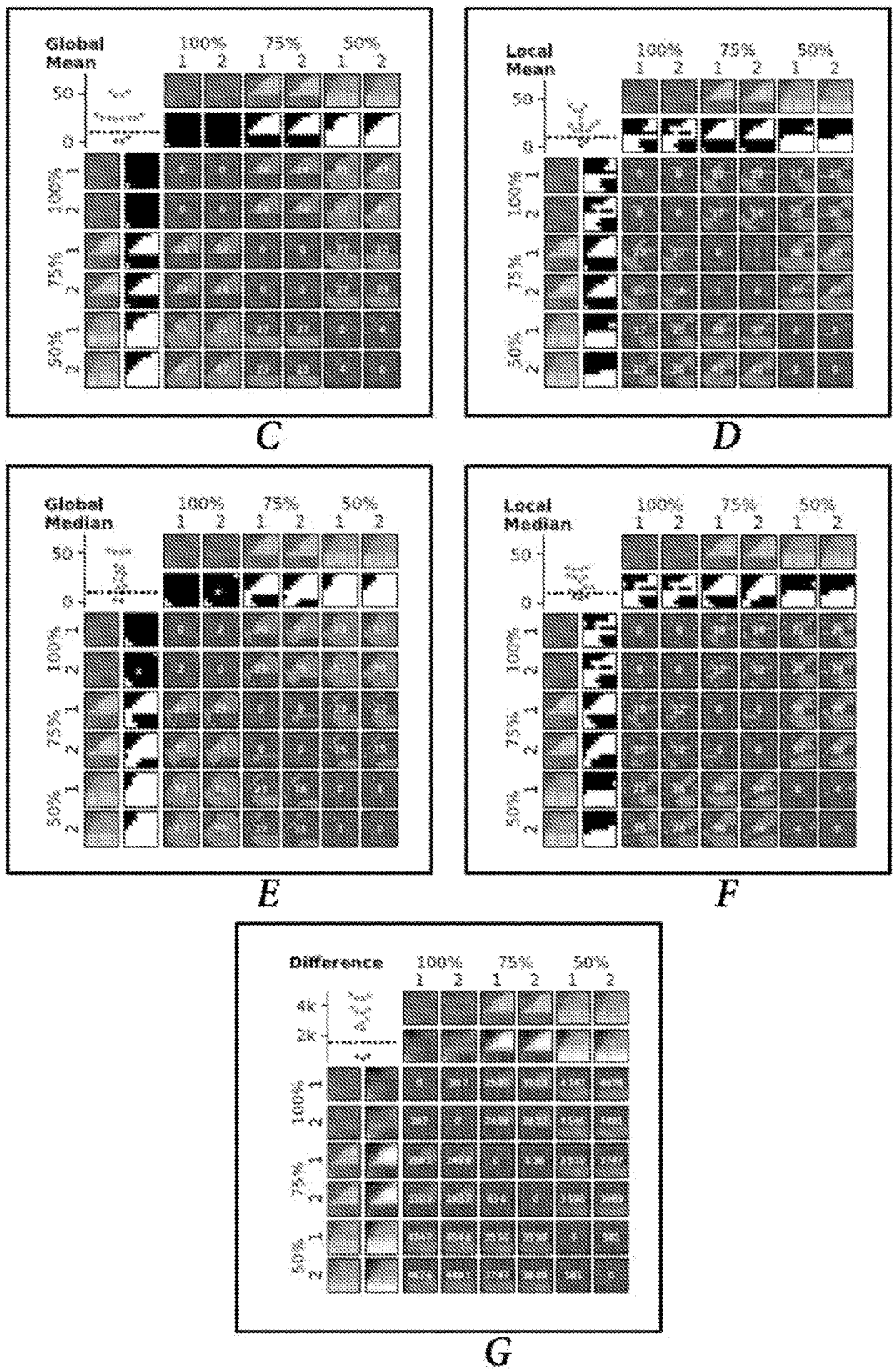
Figure 8:
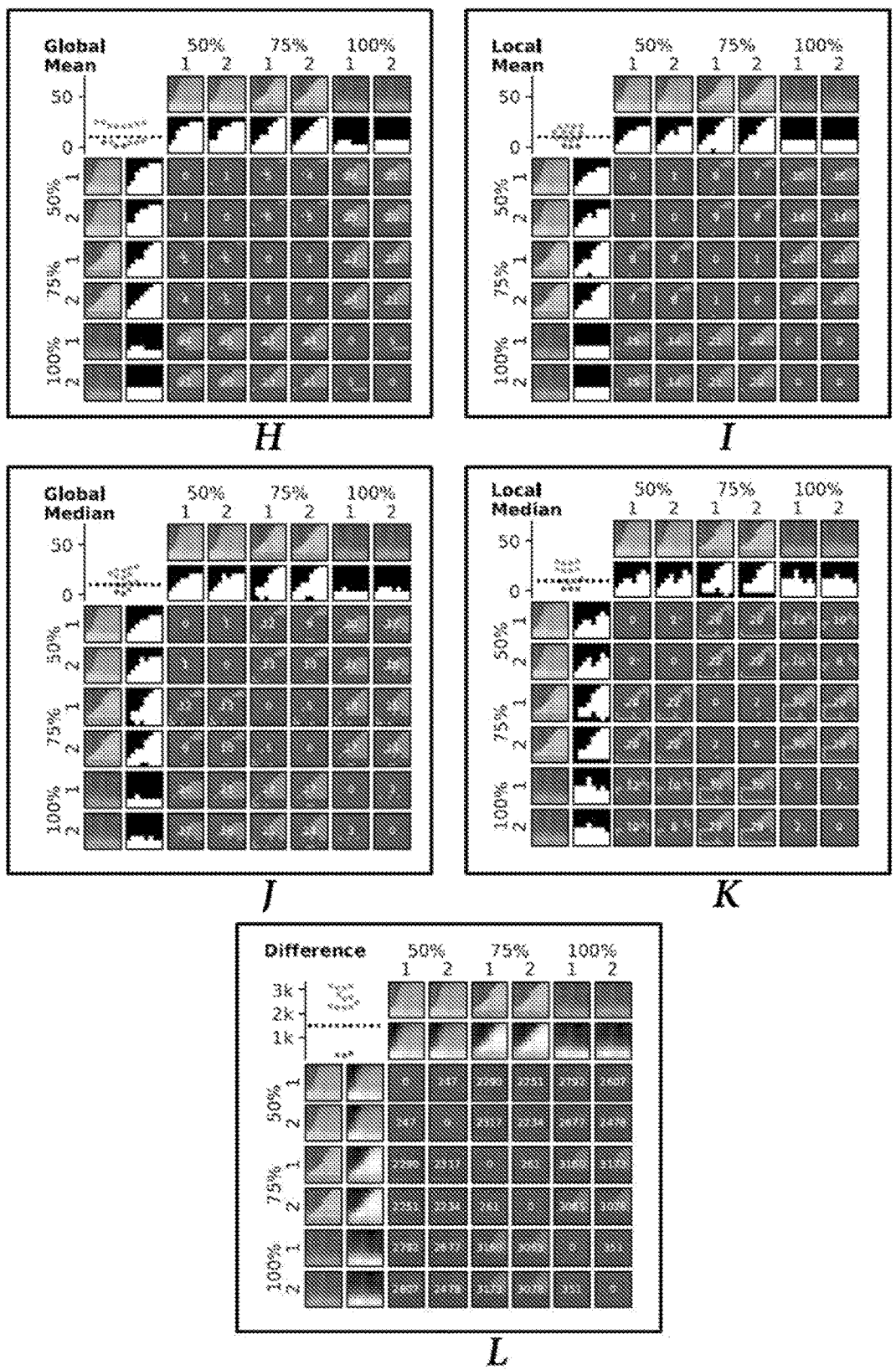
Figure 8:
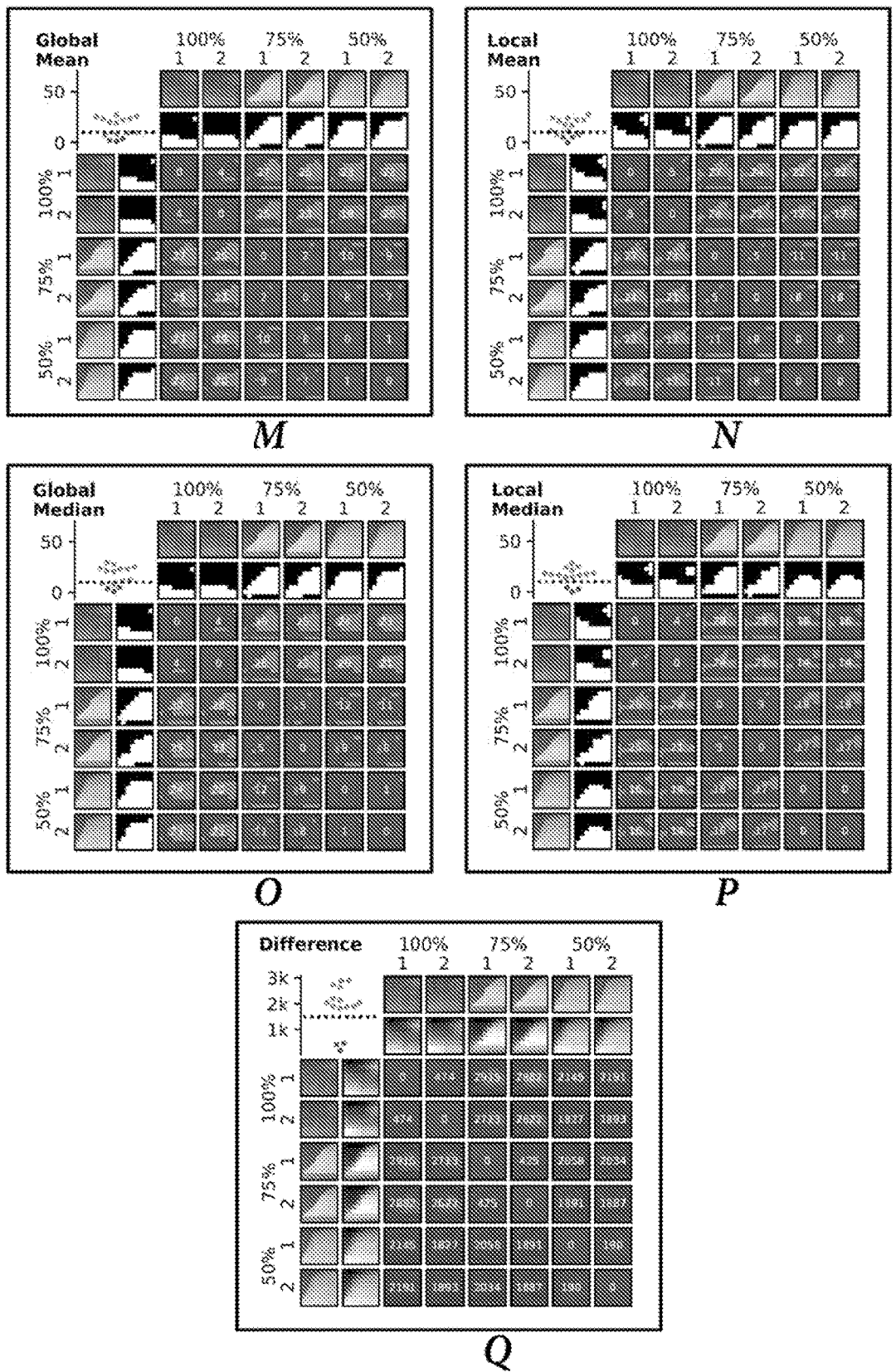
Figure 8:
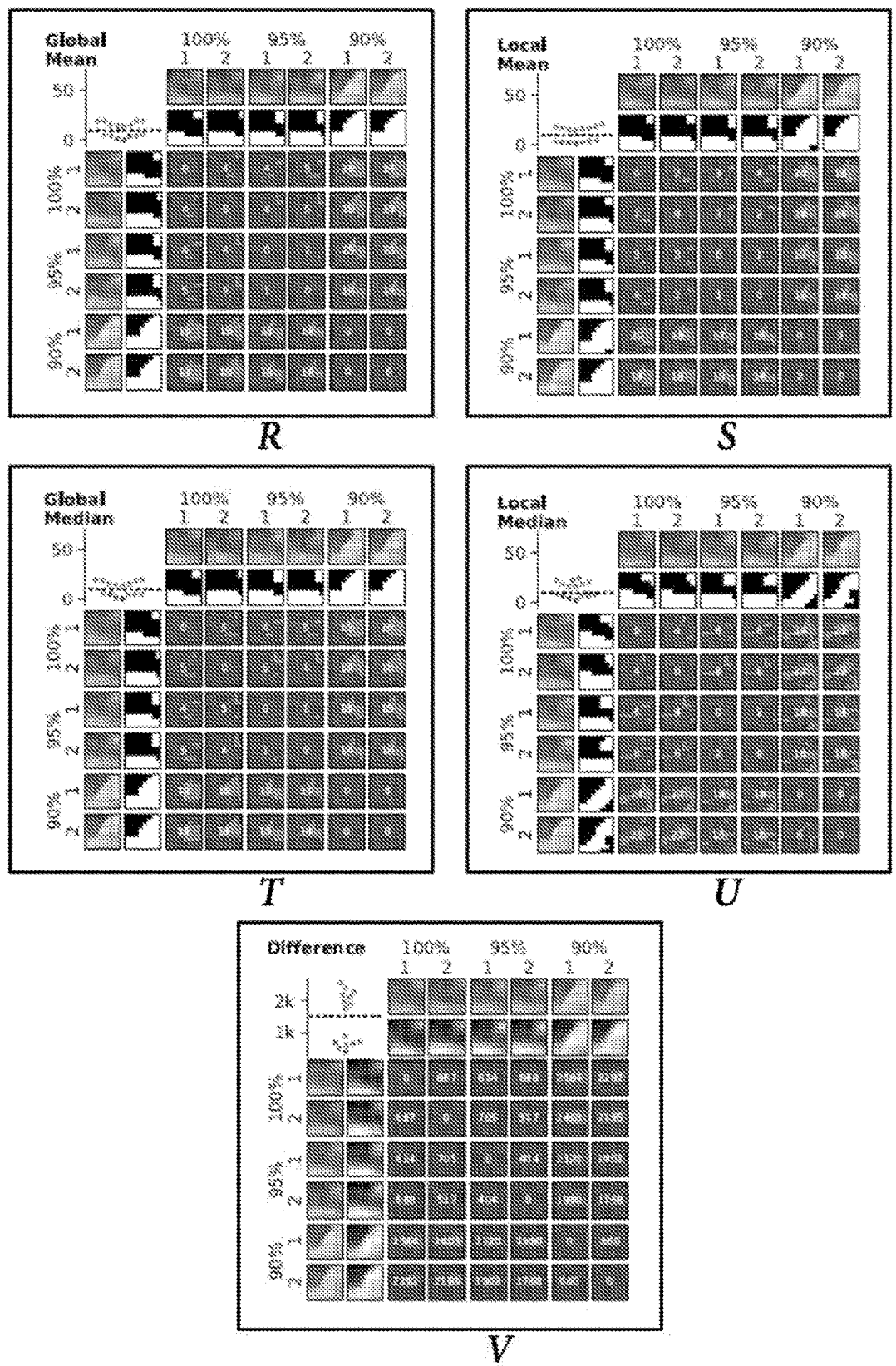
Figure 8:
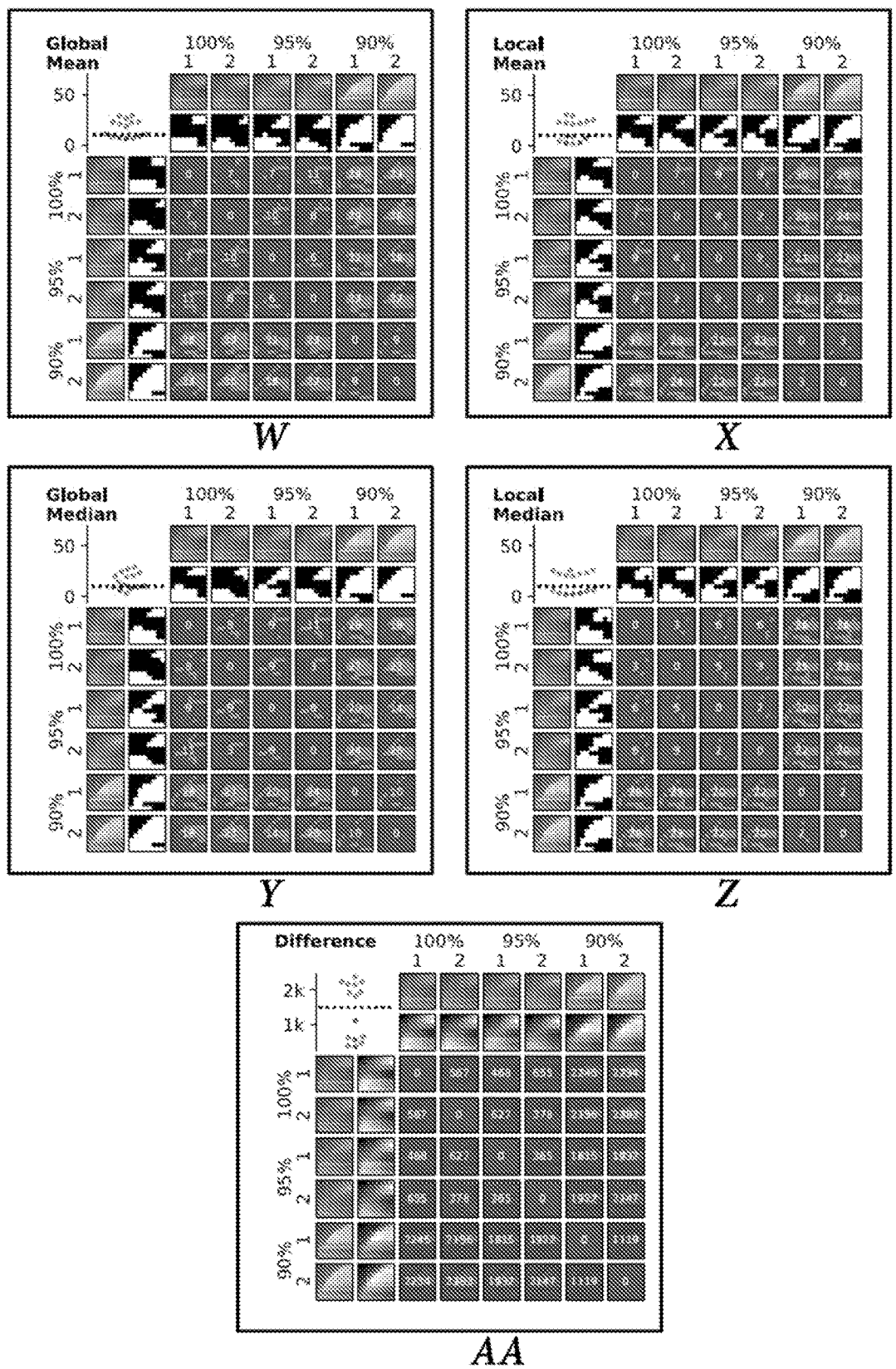
Figure 8:
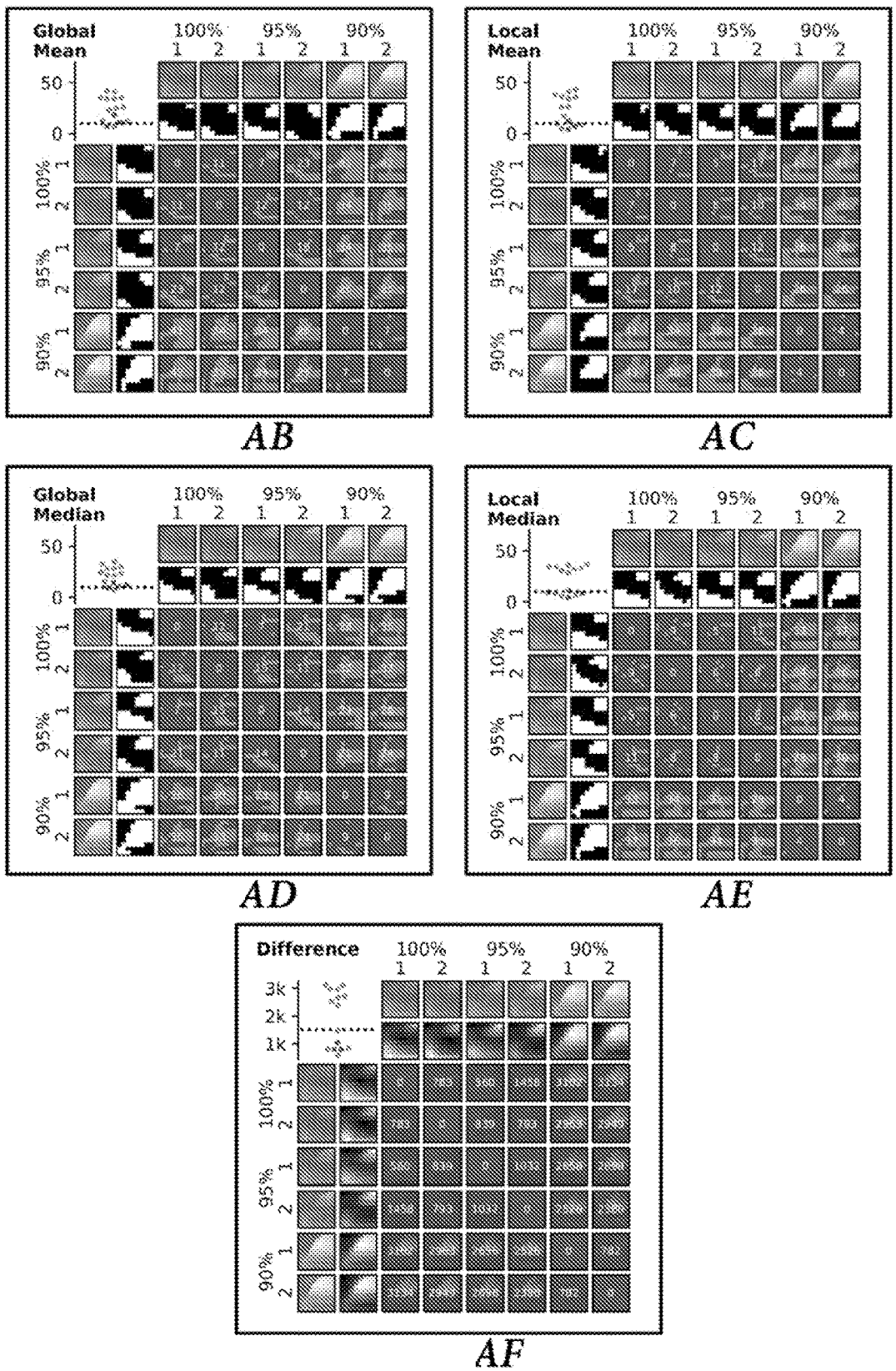

To explore the sensitivity of the chronological fingerprint technique, we repeated the cold medicine analysis above but with smaller differences between the different dilutions: 90%, 95% and 100% (vol/vol). For this experiment, we found that the image differences comparison method provided the clearest results, shown in FIG. 8 (B). As expected, within each dilution, the two samples' chronological fingerprints are very similar: the two samples of 100% medicine have image difference scores of only 687, the two samples of 95% medicine have scores of 404, and the two samples of 90% medicine have scores of 660. These scores are all less than the ~1500 threshold that we observed separates image differences scores of identical (<1500) and different (>1500) samples. Also as expected, two different dilutions' chronological fingerprints were very different: the 90% medicine had image differences scores from 2195 to 2564 when compared to the 100% medicine and 1768 to 2120 when compared to the 95% medicine. However, the 95% and 100% medicines had indistinguishable chronological fingerprints—their image differences scores ranged from 517 to 888, which are below the ~1500 threshold and therefore erroneously identified as identical. In summary, the results in FIG. 8 (A-AF) show that our chronological fingerprint method can identify samples of this cold medicine that have been diluted by as little as 10%. Additional chronological fingerprint experiments for the 90%, 95%, and 100% (vol/vol) dilutions of cough medicine in water, as well as the different analysis methods for the experiment are shown in FIG. 8 (R-AF).

Example 3.3 Case Study—Identifying Toxic Pharmaceutical Products

Figure 9:
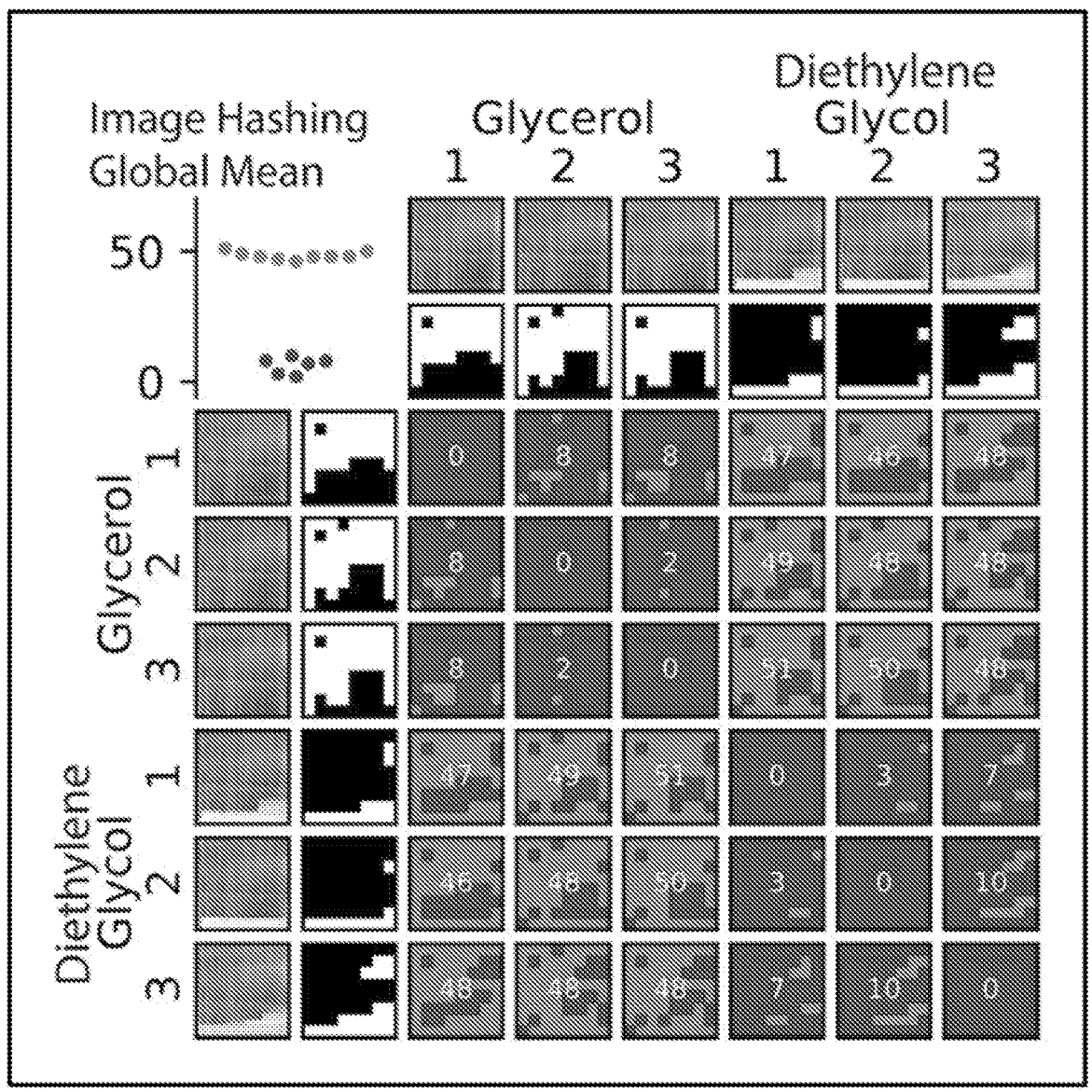
FIG. 9. Distinguishing toxic and nontoxic pharmaceutical ingredients using chronological fingerprints. Chronological fingerprints of three samples of toxic diethylene glycol and three samples of nontoxic glycerol were analyzed using the image hashing technique with the global mean pixel value as the threshold. The three glycerol chronological fingerprint hashes were nearly identical (differing by 8 or fewer bits), as were the three diethylene glycol hashes (differing by only 3 to 10 bits). However, all the glycerol chronological fingerprint hashes were significantly different from all of the diethylene glycol hashes (differing by 46 to 51 bits out of a maximum of 64). These results confirm that these substances can be easily distinguished by their chronological fingerprints.

To determine whether the chronological fingerprint technique and system could distinguish toxic diethylene glycol from nontoxic glycerol, a fluidic chip was filled with three samples each of both substances, the chip partially immersed in liquid nitrogen, and chronological fingerprints obtained from the video recording of the chip. The chronological fingerprints were then analyzed using the image hashing technique with the global mean pixel value used as the threshold. The results, shown in FIG. 9, confirm that all the glycerol chronological fingerprint hashes are very similar fingerprints, never differing by more than 8 bits, as are all the diethylene glycol chronological fingerprint hashes, never differing by more than 10 bits. However, the glycerol chronological fingerprint hashes are significantly different from the diethylene glycol chronological fingerprint hashes, differing by at least 46 bits. These results confirm that the chronological fingerprint method can easily distinguish between toxic diethylene glycol and nontoxic glycerol.

Example 3.4 Comparing Chronological Fingerprints with Particles

Figure 10:
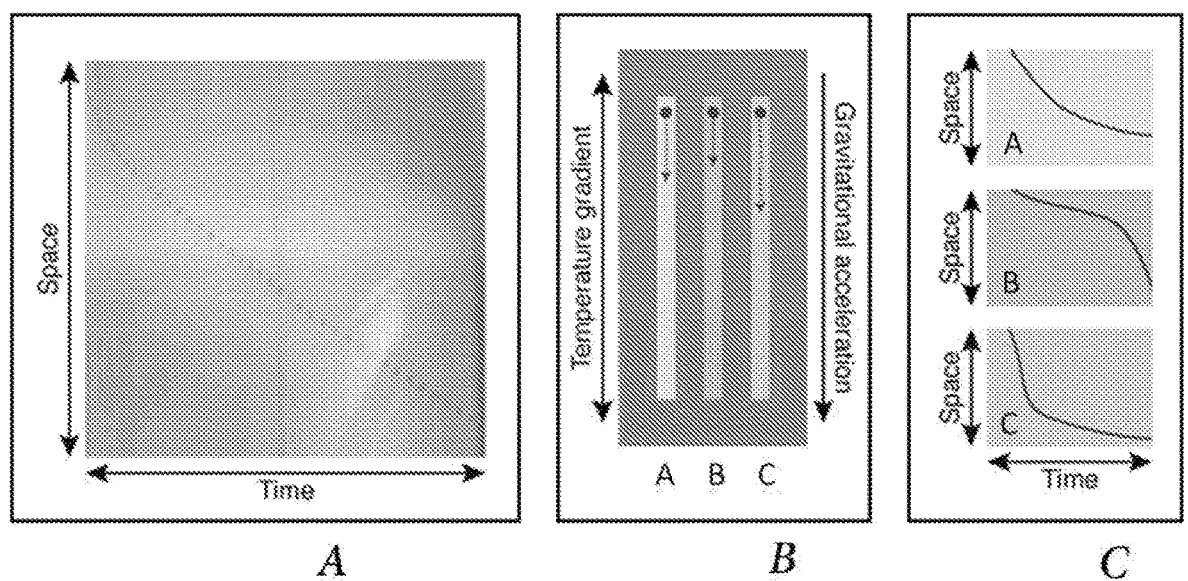
FIG. 10. Using particles and gravitational perturbations to discriminate substances in chronological fingerprints. (A) A chronological fingerprint of a substance obtained while a metal bead travels through the substance under the influence of gravity. The diagonal curve across the chronoprint records the bead's trajectory through the sample. (B) Three different substances (labeled "A," "B," and "C") are loaded into channels along with a metal bead. Since a substance's properties like viscosity and density vary by the substance's chemical composition and by temperature, the time-dependent trajectory of a particle through the substance may also vary from one substance to another. (C) The resulting differences in particle trajectories are recorded in the substances' chronoprints and can be used to distinguish one substance from another.

To test the ability to observe a physical perturbation, after the fluidics chip was loaded with water a 1/32-inch, or 793.75 μm, diameter steel bead was loaded into the upper reservoir with the chip placed in a horizontal position such that the bead would not move. Then the fluidics chip was tilted upright into the brace to demonstrate the capability. The camera recorded the fluid response, specifically the transitioning the metal bead through the substance, shown in FIG. 10 (A), as expected the bead has a linear trajectory after an initial acceleration indicating a constant viscosity (no temperature perturbation). Since different substances behave differently in response to a thermal perturbation the path of the bead through the substance may also vary, some possible examples are outlined in FIG. 10 (B-C).

Unless otherwise indicated, all numbers expressing quantities of ingredients, properties such as molecular weight, reaction conditions, and so forth used in the specification and claims are to be understood as being modified in all instances by the term "about." As used herein, the term "about" means that the item, parameter or term so qualified encompasses a range of plus or minus ten percent above and below the value of the stated item, parameter or term. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed considering the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the embodiments disclosed in the present disclosure.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 90%" includes "90%." In some embodiments, at least 95% pure includes 96%, 97%, 98%, 99%, and 100% purity as compared to a reference.

Any titles or subheadings used herein are for organization purposes and should not be used to limit the scope of embodiments disclosed herein.

What is claimed is:

1. A method of validating an identity of one of more component(s) in a substance, comprising:
    obtaining the substance;
    placing the substance in a plenum with a sealed bottom;
    exposing the substance to a perturbation;
    digitally recording time-dependent changes over a period of time in the substance, wherein the changes are recorded before, during and after exposing the substance to the perturbation;
    producing a chronological fingerprint image of the changes, where the chronological fingerprint image is a digital multi-dimensional image of the changes as a function of time, wherein the chronological fingerprint image represents the digitally recorded time-dependent changes measured before, during and after exposing the substance to the perturbation; and
    comparing the chronological fingerprint image to chronological fingerprint images for known substances to validate the identity of the one or more component(s) in the substance being measured.

2. The method of claim 1, where the step of comparing comprises comparing the chronological fingerprint image to chronological fingerprint images for known substances via feature tracing, image differences, or image hashing.

3. The method of claim 1, where the known substances comprises known substances measured in a same experiment.

4. The method of claim 1, where the known substances comprise known substances previously measured, from a database of chronological fingerprint images.

5. The method of claim 1, where the known substances comprise both known substances measured in the same experiment and known substances previously measured, from a database of chronological fingerprint images.

6. The method of claim 1, where the perturbation comprises a thermal perturbation, a force perturbation, or a physical perturbation.

7. The method of claim 1, further comprising a step of converting the chronological fingerprint image to a binary chronological fingerprint image before comparing.

8. The method of claim 7, further comprising a step of tracing features of the binary chronological fingerprint image before comparing, where the comparing is done on the traced features.

9. The method of claim 1, further comprising a step of calculating a sum of pixel-by-pixel differences between two chronological fingerprint images.

* * * * *